US009995680B2

(12) United States Patent
Easley et al.

(10) Patent No.: US 9,995,680 B2
(45) Date of Patent: Jun. 12, 2018

(54) THERMALLY RESOLVED MOLECULE ASSAYS

(71) Applicant: Auburn University, Auburn, AL (US)

(72) Inventors: Christopher J. Easley, Auburn, AL (US); Joonyul Kim, Opelika, AL (US); Juan Hu, Auburn, AL (US); Mark D. Holtan, Auburn, AL (US); Subramaniam Somasundaram, Auburn, AL (US); Curtis Shannon, Auburn, AL (US)

(73) Assignee: Auburn University, Auburn, AL (US)

( * ) Notice: Subject to any disclaimer, the term of this patent is extended or adjusted under 35 U.S.C. 154(b) by 107 days.

(21) Appl. No.: 14/932,678

(22) Filed: Nov. 4, 2015

(65) Prior Publication Data

US 2016/0131604 A1 May 12, 2016

Related U.S. Application Data

(60) Provisional application No. 62/114,251, filed on Feb. 10, 2015, provisional application No. 62/074,939, filed on Nov. 4, 2014.

(51) Int. Cl.
C12Q 1/68 (2006.01)
C07H 21/00 (2006.01)
G01N 33/53 (2006.01)
G01N 21/64 (2006.01)
G01N 33/542 (2006.01)

(52) U.S. Cl.
CPC ....... *G01N 21/6428* (2013.01); *C12Q 1/6818* (2013.01); *G01N 33/5308* (2013.01); *G01N 33/542* (2013.01); *G01N 2021/6432* (2013.01)

(58) Field of Classification Search
CPC ........... C12Q 1/68; C07H 21/00; C12P 19/34; G01N 33/53; A61K 39/395
See application file for complete search history.

(56) References Cited

U.S. PATENT DOCUMENTS

| | | | |
|---|---|---|---|
| 2004/0175752 A1 | 9/2004 | Schaffer et al. | |
| 2009/0042205 A1 | 2/2009 | Didenko | |
| 2012/0134978 A1 | 5/2012 | Agar | |
| 2012/0295283 A1* | 11/2012 | Barrett | C07D 519/00 435/7.8 |
| 2013/0101988 A1* | 4/2013 | Getman | C12Q 1/6865 435/5 |
| 2014/0102915 A1* | 4/2014 | Hu | C12Q 1/6804 205/777.5 |

FOREIGN PATENT DOCUMENTS

WO 2010132813 A2 11/2010

OTHER PUBLICATIONS

Huang et al., Plos One 6(4) : e19206 (2011).*
Lay et al. Clinical Chemistry 43(12) : 2262 (1997).*
Lyon, E. Expert Opinions in Molecular Diagnosis 1(1) : 92 (2001).*
Szilvasi et al., Clinical Biochemistry 38 :727 (2005).*
Varga et al., J. of Virological Methods 123 : 213 (2005).*
Wittwer et al., Clinical Chemistry 49(6) :853 (2003).*
Branigan, E., et al., "Quantification of free cysteines in membrane and soluble proteins using a fluorescent dye and thermal unfolding." Nature Protocols (online), Nov. 2013, retrieved Dec. 28, 2015, 8:11.
Cozzani V. et al., "A new method to determine the composition of biomass by thermogravimetric analysis." The Canadian journal of chemical engineering (online), Feb. 1997, retrieved Dec. 28, 2015, 75:1.
Mao S., et al., "Optical lock-in detection of FRET using synthetic and genetically encoded optical switches." Biophysical Journal (online), Jun. 1, 2008, retrieved Dec. 28, 2015, 94:11.
International Search Report and Written Opinion for PCT/US15/59020 dated Jan. 29, 2016.
Heyduk, Ewa, et al., "Molecular pincers—new antibody-based homogenous protein sensors," Anal. Chem. 2008, 30:13,5152-5159.
Kim, J., et al., 2010, Anal. Chem. Kim, J.; Hu, J.; Sollie, R.; Easley, C.; Improvement of Sensitivity and Dynamic Range in Proximity Ligation Assays by Asymmetric Connector Hybridization, 2010, Anal. Chem., 6976-6992.
K. W. Plaxco and H. T. Soh, Switch-based biosensors: a new approach towards real-time, in vivo molecular detection, Trends Biotechnol, 2011, 29, 1-5.
Hu, et al., Quantification of Femtomolar Protein Levels via Direct Readout with the Electrochemical Proximity Assay. J Am Chem Soc, 2012, 134, 7066-7072.
Hu, et al., A Reusable Electrochemical Proximity Assay for Highly Selective, Real-Time Protein Quantification in Biological Matrices, J Am Chem Sac, 2014, 136, 8467-8474.
Fredriksson, et al., Protein detection using proximity-dependent DNA ligation assays. Nat Biotechnol 2002; 20:473-477
DeJournette, et al., Creating Biocompatible Oil-Water Interfaces without Synthesis: Direct Interactions between Primary Amines and Carboxylated Perfluorocarbon Surfactants. Am. Chem. Soc. 2013, 10556-10564.
Ren, et al., Ratiometric electrochemical proximity assay for sensitive one-step protein detection. Scientific Reports 4:4360, 2014, 1-6.
Rosen, et al., Template-directed covalent conjugation of DNA to native antibodies, transferrin, and other metal-binding proteins, Nature Chemistry 6, 2014, 804-809.
Gulaboski, et al., Protein-film voltammetry: A theoretical study of the temperature effect using square-wave voltammetry. Biophysical Chemistry 137 (2008), 49-55.
Wohlgamuth, et al., Temperature Dependence of Electrochemical DNA Charge Transport: Influence of a Mismatch, Am. Chem. Soc. 2012, 1462-1467.
Yang, et al., Accurate Zygote-Specific Discrimination of Single-Nucleotide Polymorphisms Using Microfluidic Electrochemical DNA Melting Curves, Angew. Chem. 2014, 126, 3227-3231.
Kim, J., et al., "Protein Quantification Using Controlled DNA Melting Transitions in Bivalent Probe Assemblies," 2015, Supporting Information, Analytical Chemistry, A-D.

(Continued)

Primary Examiner — Ethan C Whisenant
(74) Attorney, Agent, or Firm — Thomas | Horstemeyer, LLP

(57) ABSTRACT

Provided herein are compositions and methods including the step of thermally scanning a sample that can be used and implemented to detect the presence of and/or concentration of a molecule in a sample.

26 Claims, 29 Drawing Sheets

(56) References Cited

OTHER PUBLICATIONS

Zhang H. et al., Assembling DNA through Affinity Binding to Achieve Ultrasensitive Protein Detection, Angew. Chem., Int. Ed. 2013, 52, 10698-10705.

Hu, J., et al., "Quantifying Aptamer-Protein Binding via Thermofluorimetric Analysis," Analytical Methods 2015, 1-3.

Xiao, et al., On the Signaling of Electrochemical Aptamer-Based Sensors: Collision- and Folding-Based Mechanisms, Electroanalysis, 2009, 21, 1267-1271.

Lundberg, et al., Homogenous antibody-based proximity extension assays provide sensitive and specific detection of low-abundant proteins in human blood, Nucleic acids research, 2011, 39:15, 1-8.

Pantoliano, et al., High-Density Miniaturized Thermal Shift Assays as a General Strategy for Drug Discovery, Journal of biomolecular screening, 2001, 6, 429-440.

Niesen, et al., the use of differential scanning fluorimetry to detect ligand interactions that promote protein stability, Nature protocols, 2007, 2, 2212-2221.

Gullberg, et al., Cytokine detection by antibody-based proximity ligation, Proc Natl Acad Sci U S A 2004;101:8420-8424.

Heyduk E, et al., Nucleic Acid-based Fluorescence Sensors for Detecting Proteins, Anal. Chem. 2005; 77:1147-1156.

Heyduk T et al. Molecular beacons for detecting DNA binding proteins, Nature Biotechnol 2002; 20:171-176.

Soderberg, et al., Characterizing proteins and their interactions in cells and tissues using the in situ proximity ligation assay. Methods 2008, 45, 227-232.

Gustafsdottir, et al., in vitro analysis of DNA-protein interactions by proximity ligation, Proc. Natl. Acad. Sci. U.S.A. 2007, 104, 3067-3072.

Nordengrahn, et al., Evaluation of a novel proximity ligation assay for the sensitive and rapid detection of foot-and-mouth disease virus. Vet. Microbiol. 2008, 127, 227-236.

Gustafsdottir, et al., Use of Proximity Ligation to Screen for Inhibitors of Interactions between Vascular Endothelial Growth Factor a and Its Receptors. U. Clin. Chem. 2008, 54, 1218-1225.

Livak, K. J. User Bulletin No. 2: ABI PRISM 7700 Sequence Detection System; PE Applied Biosystems: Foster City, CA, 1997; pp. 11-15.

Hu, et al., Homogeneous Assays of Second Messenger Signaling and Hormone Secretion Using Thermofluorimetric Methods That Minimize Calibration Burden, Anal. Chem. 2017, 89, 8517-8523.

Somasundaram, et al., Understanding signal and background in a thermally resolved, single-branched DNA assay using square wave voltammetry, Anal. Chem. 2018, manuscript in press, 1-9.

\* cited by examiner

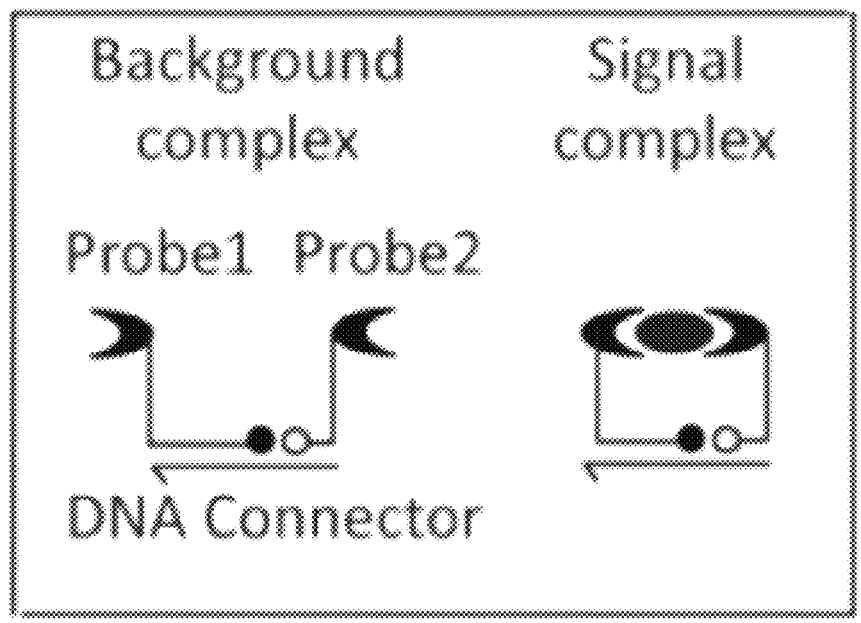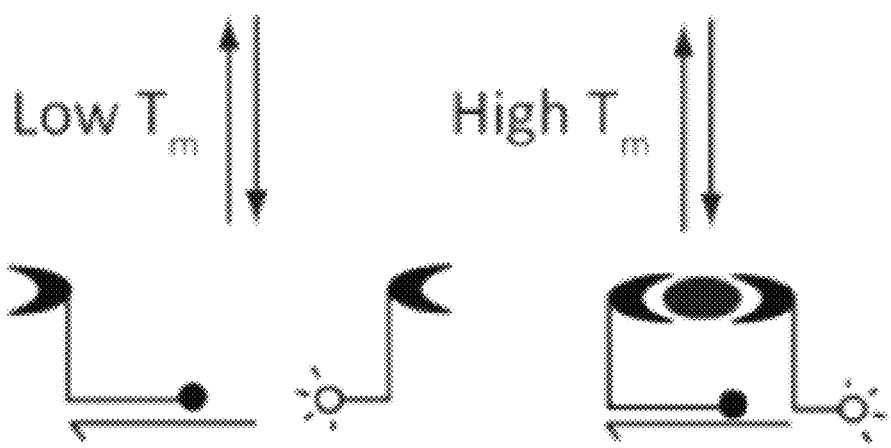
FIG. 12

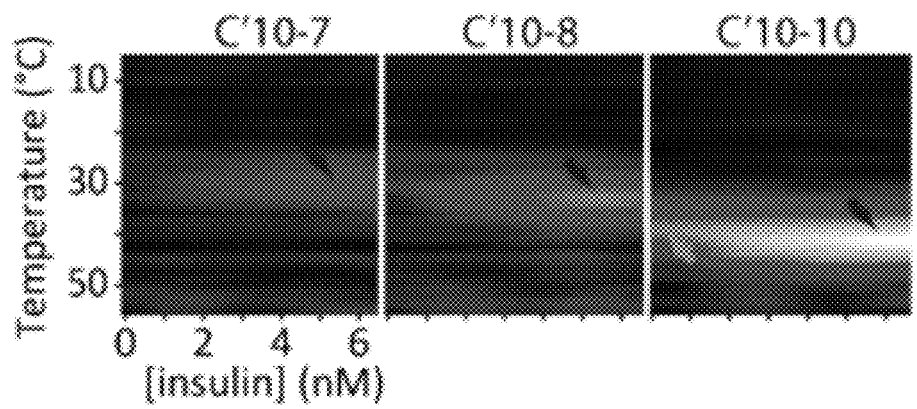
FIG. 15A   FIG. 15B   FIG. 15C
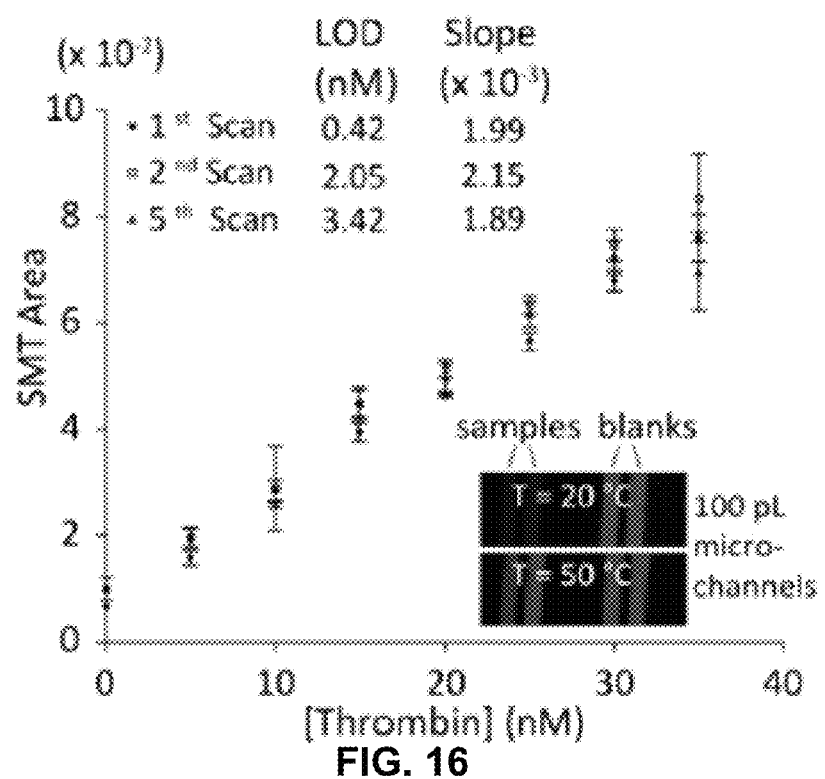
FIG. 16

| Experiment | Seq. Name and ID No. | Seq. 5'→3' with IDT codes) |
|---|---|---|
| Thrombin TFAB | Thr1_BFQ (SEQ ID NO: 1) | <u>CAGTCCGTGGTAGGGCAGGTTGGGGTGACTTTT</u>ACTTTCTGCACGACACTTTGGAACAGC/3IABkFQ/ |
| | Thr2_TAMARA (SEQ ID NO: 2) | /55-TAMK/AATAACGTCAGAATCGTACTCGGG<u>TGTGACTACTGGTTGGTGAGGTTGGGTAGTCACAAA</u> |
| | C9-12 (SEQ ID NO:3) | GACGTTATTGCTGTTCCAAAG |
| | C8-12 (SEQ ID NO:4) | ACGTTATTGCTGTTCCAAAG |
| | C7-12 (SEQ ID NO:5) | CGTTATTGCTGTTCCAAAG |
| Insulin TFAB | AbA_BHQ2 (SEQ ID NO: 6) | /5AmMC6//iSp18/TCGTGGAACTATCTAGCGGTGTACGTGAGTGGGCATGTAGCAAGAGG/3BHQ_2/ |
| | AbB_TYE665 (SEQ ID NO: 7) | /5TYE665//iSp18/TCGTGGAACTATCTAGCGGTGTACGTGAGTGGGCATGAGCAAGAGG/3IABkFQ/ |
| | AbA_BFQ (SEQ ID NO: 8) | /5AmMc6//iSp18/TCGTGGAACTATCTAGCGGTGTACGTGAGTGGGCATGTAGCAAGAGG/3IABkFQ/ |
| | AbB_TAMARA (SEQ ID NO: 9) | /55-TAMK/GTCATCATTCGAATCGTACTGCAATCGGGTATTAGGCTA/iSp18//3AmMC6T/ |
| | C'10-10 (SEQ ID NO: 10) | GAATGATGACCCTCTTGCTA |
| | C'10-8 (SEQ ID NO: 11) | ATGATGACCCTCTTGCTA |
| | C'10-7 (SEQ ID NO:12) | TGATGACCCTCTTGCTA |
| Isothermal thrombin assay with a bivalent probe | Thr1_BFQ (SEQ ID NO: 13) | <u>CAGTCCGTGGTAGGGCAGGTTGGGGTGACTTTT</u>ACTTTCTGCACGACACTTTGGAACAGC/3IABkFQ/ |
| | Thr2_TAMARA (SEQ ID NO: 14) | /55-TAMK/AATAACGTCAGAATCGTACTCGGG<u>TGTGACTACTGGTTGGTGAGGTTGGGTAGTCACAAA</u> |
| | C15-15 (SEQ ID NO: 15) | GATTCT*U*ACGTTATTGCTGTTCCAAAG*U*GT |
| | C8-12 (SEQ ID NO: 16) | ACGTTATTGCTGTTCCAAAG |

Underlining indicates aptamer.
Bold and italics indicates deoxyuridines.

FIG. 23

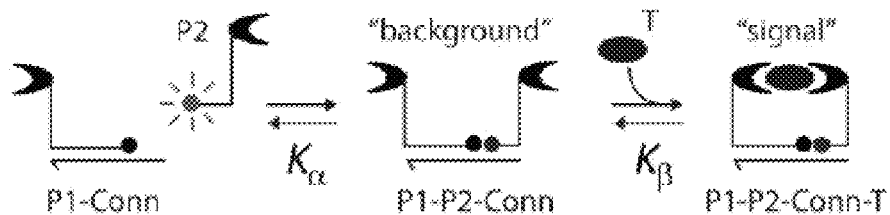

$$K_\alpha = \frac{[P1 - Conn][P2]}{[P1 - P2 - Conn]} \quad K_\beta = \frac{[P1 - P2 - Conn][T]}{[P1 - P2 - Conn - T]}$$

Assumptions during background melting
1. $[P1 - P2 - Conn - T] \cong [T]_t$
2. $\Delta[P1 - P2 - Conn - T] \cong 0$ $$K_\alpha = \frac{[P1 - Conn][P2]}{[P1 - P2 - Conn]} = \frac{[P2]^2}{[P2]_t - [P2] - [T]_t}$$

$$Ln(K_\alpha) = Ln\left(\frac{[P2]^2}{[P2]_t - [P2] - [T]_t}\right) = -\frac{\Delta H_\alpha}{R}\left(\frac{1}{T}\right) + \frac{\Delta S_\alpha}{R}$$

Assumptions during signal melting
1. $[P1 - P2 - Conn] \cong 0$ $$K_\alpha K_\beta = \frac{[P1 - Conn][P2][T]}{[P1 - P2 - Conn - T]} = \frac{[P2]^2([T]_t - [P2]_t + [P2])}{[P2]_t - [P2]}$$

$$Ln(K_\beta) = Ln\left(\frac{[P2]^2([T]_t - [P2]_t + [P2])}{[P2]_t - [P2]}\right) - Ln(K_\alpha)$$

$$= -\frac{\Delta H_\beta}{R}\left(\frac{1}{T}\right) + \frac{\Delta S_\beta}{R}$$

FIG. 30

Experiments

Model

Temperature (°C)

THERMALLY RESOLVED MOLECULE ASSAYS

CROSS-REFERENCE TO RELATED APPLICATIONS

This application claims the benefit of U.S. Provisional Application Ser. No. 62/074,939 filed on Nov. 4, 2014, having the title "Methods and Instrumentation for Thermally Resolved Protein Assays", the entirety of which is incorporated herein by reference. This application also claims the benefit of U.S. Provisional Application Ser. No. 62/114,251 filed on Feb. 10, 2015, having the title "Instrumentation for Thermally Resolved Protein Assays", the entirety of which is incorporated herein by reference.

STATEMENT REGARDING FEDERALLY SPONSORED RESEARCH OR DEVELOPMENT

This invention was made with government support under grant numbers CBET 1067779 and CBET 1403495 awarded by the National Science Foundation. This invention was made with government support under grant number R01DK093810 awarded by the National Institutes of Health. The government has certain rights in this invention.

SEQUENCE LISTING

This application contains a sequence listing filed in electronic form as an ASCII.txt file entitled 02339497.txt, created on Jan. 15, 2016 and having a size of 3801 bytes. The content of the sequence listing is incorporated herein in its entirety.

BACKGROUND

Assays that can specifically detect and/or quantify the amount of a molecule in a sample have a vast applicability. They are central tools within the ever expanding field of personalized medicine and can be the first line of defense against chemical and bioterrorism. As such there is an omnipresent need for improved molecule, including protein, detection and quantification assays.

SUMMARY

Provided herein are methods of target molecule detection including the steps of contacting a sample with a first probe, wherein the first probe is configured to bind a target molecule, contacting the sample with a second probe, wherein the second probe is configured to bind the target molecule, forming a signal complex, thermally scanning the signal complex to form a temperature melting curve, the temperature melting curve containing a first melting temperature peak, where the first melting temperature peak corresponds to the melting temperature of the signal complex, and detecting the target molecule via measuring a characteristic of the first melting temperature peak. The methods can further include the step of quantifying the amount of signal complex by the peak area of the first melting temperature peak. The methods can further include the step of forming a background complex and wherein the temperature melting curve further comprises a second melting temperature peak, where the second temperature melting peak corresponds to the melting temperature of the background complex. The first probe can be selected from the group of aptamers, antibodies or fragments thereof, proteins, and oligonucleotides. The second probe can be selected from the group of aptamers, antibodies or fragments thereof, proteins, and oligonucleotides.

In some embodiments, the first probe and the second probe can be each directly bound to the target molecule in the signal complex. The first probe and the second probe can each be independently selected from the group of aptamers, antibodies or fragments thereof, proteins, and oligonucleotides. The methods can further include the step of contacting the signal complex with an intercalating agent. The step of thermally scanning can further include measuring a signal produced by the intercalating agent. In some embodiments, the first probe, the second probe, or each of the first and the second probes comprise an optically active molecule. The step of thermally scanning can further include measuring a signal produced by the optically active molecule. In some embodiments, the first probe comprises a Förster resonance energy transfer (FRET) donor molecule or a FRET acceptor molecule. The second protein probe can contain a FRET donor or a FRET acceptor molecule, where the first protein probe and the second protein probe are not both FRET donor or FRET acceptor molecules. The step of thermally scanning can further include measuring a signal produced by the FRET donor molecule.

In some embodiments, the methods can include the step of contacting the sample with a proximity oligonucleotide. The first probe can be configured to bind the target molecule and the proximity oligonucleotide. The second probe can be configured to bind the target protein and the proximity oligonucleotide, and the first and the second probes can form a paired bivalent probe. The first probe and the second probe can each contain a protein binding moiety independently selected the group of: aptamers, antibodies or fragments thereof, proteins, and oligonucleotides. The binding moiety can be an antibody or a fragment thereof and the antibody or a fragment thereof can further contain a connector oligonucleotide, where the connector oligonucleotide can be coupled to the antibody or fragment thereof and can be configured to bind the proximity nucleotide. The first probe can contain a quencher molecule. In some embodiments, the second probe can contain an optically active molecule. The step of thermally scanning can further include measuring a signal produced by the optically active molecule. In some embodiments, the first probe or the second probe can contain a FRET donor molecule. The first probe or the second probe can contain a FRET acceptor molecule, where the first probe and the second probe are not both FRET acceptor molecules or FRET donor molecules. The step of thermally scanning can further contain measuring a signal produced by the FRET donor molecule.

In some embodiments, the proximity oligonucleotide can be coupled to an electrically conductive substrate. The first probe, the second probe, or each of the first probe and the second probe can contain a redox-active molecule. The step of thermally scanning can further include measuring the current produced by the electrically conductive substrate.

In some embodiments, the methods can include the step of contacting the sample with a connector oligonucleotide, where the connector oligonucleotide can be configured to bind the proximity oligonucleotide. The second probe can be configured to bind the target molecule and the connector oligonucleotide. The proximity oligonucleotide can be coupled to an electrically conductive substrate. The first probe, the second probe, the connector oligonucleotide, or combinations thereof, can further contain a redox active molecule. The step of thermally scanning can further include measuring the current produced by the electrically conductive substrate.

In some embodiments, the first probe and the second probe are each oligonucleotides. The first probe or the second probe can be coupled to an electrically conductive substrate. The first probe, the second probe, or each of the first probe and the second probe can further contain a redox-active molecule. The step of thermally scanning can further include measuring the current produced by the electrically conductive substrate.

In some embodiments, the characteristic of the first melting temperature peak can be compared to a predetermined value for the characteristic of the first melting temperature peak.

The methods can further include the step of measuring a characteristic of the second melting temperature peak. The characteristic of the first melting temperature peak can be compared to a predetermined value for the characteristic of the first melting temperature peak. The characteristic of the second melting temperature peak can be compared to a predetermined value for the characteristic of the second melting temperature peak. The characteristic of the second melting temperature peak can be compared to a predetermined value for the characteristic of the second melting temperature peak.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 12 shows a schematic depicting an embodiment of a thermofluorimetric assay using bivalent probes (TFAB).

FIGS. 15A-15C show heat maps for insulin TFABs using C'10-7 (FIG. 15A), C'10-8 (FIG. 15B), or C'10-10 (FIG. 15C) length connectors.

FIG. 16 is a graph demonstrating SMT peak area was proportional to protein concentration, and repeated thermal scanning confirmed protein stability. Inset image shows microfluidic TFAB in 100 pL channels.

FIG. 23 shows a table showing single-stranded DNA (ssDNA) sequences used in the TFAB study. Strategically placed deoxyuridines in the C15-15 connector sequence permit enzymatic cleavage of the DNA strand by the Uracil DNA Excision Mix; deoxyuridines in the sequence are indicated with bolding and italicizing.

FIG. 30 shows details of the calculation of $K_\alpha$ and $K_\beta$ formula for the mathematical model shown in FIG. 20.

DETAILED DESCRIPTION

Figure 1:
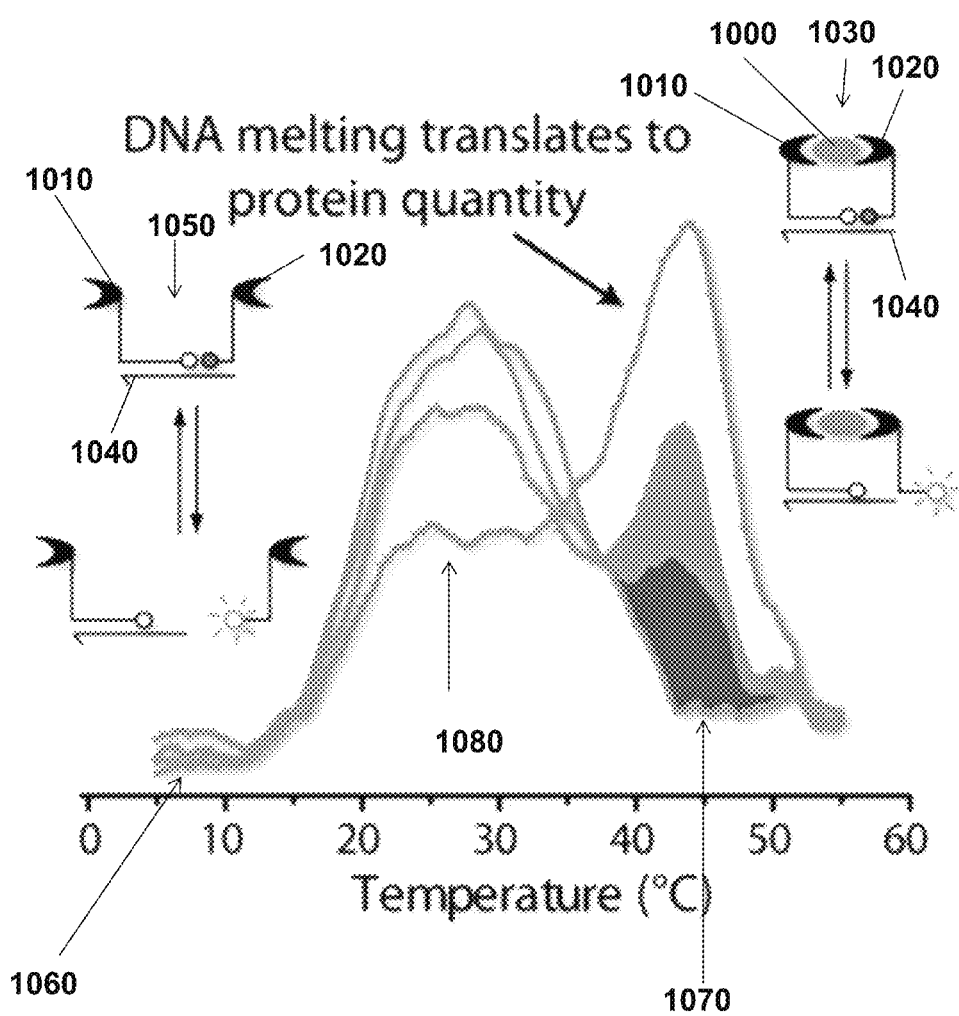
FIG. 1 shows an embodiment of a thermally resolved assay.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

As used herein, "specific binding," "specifically bound," and the like, refer to binding that occurs between such paired species as nucleotide/nucleotide, polynucleotide/polynucleotide, enzyme/substrate, receptor/agonist, antibody/antigen, and lectin/carbohydrate that can be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. "Specific binding" can be characterized by the binding of one member of a pair to a particular species and to no other species within the family of compounds to which the corresponding member of the binding member belongs. "Specific binding" can also occur when enough binding of one member of a pair to a particular species occurs such that the binding of the member and the particular species can be deemed statistically significant as compared to the amount of binding that occurs between the one member and non-specific binding species. In other words, "specific binding" also refers to the binding between one member of a pair to a particular species that occurs at such a rate or an amount so that the signal to noise ratio allows detection of this binding interaction amongst all other binding interactions that occur with the one member of the pair. Thus, for example, an antibody preferably binds to a single epitope and to no other epitope within the family of proteins or a polynucleotide preferably binding its perfect complementary polynucleotide as opposed to binding a partial complementary polynucleotide.

As used herein, "peptide" refers to two or more amino acids where the alpha carboxyl group of one amino acid is bound to the alpha amino group of another amino acid. Strings of 10 or more amino acids are also referred to herein as "polypeptides" or "proteins".

As used herein, "polypeptides" or "proteins" are amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, "gene" refers to a hereditary unit corresponding to a sequence of DNA that occupies a specific location on a chromosome and that contains the genetic instruction for a characteristic(s) or trait(s) in an organism. "Gene" also refers to the specific sequence of DNA that is transcribed into an RNA transcript that can be translated into a polypeptide or be a catalytic or non-translated RNA molecule including but not limited to tRNA, siRNA, piRNA, miRNA, lncRNA, and shRNA.

As used herein, "deoxyribonucleic acid (DNA)" and "ribonucleic acid (RNA)" generally refer to any polyribonucleotide or polydeoxribonucleotide, which can be unmodified RNA or DNA or modified RNA or DNA. RNA can be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), microRNA (miRNA), long non-coding RNA (lncRNA), or ribozymes.

As used herein, "nucleic acid sequence" and "oligonucleotide" also encompasses a nucleic acid and polynucleotide as defined above.

As used herein, "DNA molecule" includes nucleic acids/polynucleotides that are made of DNA.

As used herein, "nucleic acid," "oligonucleotide," and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, polynucleotide as used herein refers to triple-stranded regions comprising RNA or DNA or both RNA and DNA. The strands in such regions can be from the same molecule or from different molecules. The regions can include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone; artificial nucleic acids can contain other types of backbones, but contain the same bases. Thus, DNAs or RNAs with backbones modified for stability or for other reasons are "nucleic acids" or "polynucleotide" as that term is intended herein.

As used herein, "about," "approximately," and the like, when used in connection with a numerical variable, generally refers to the value of the variable and to all values of the variable that are within the experimental error (e.g., within the 95% confidence interval for the mean) or within .+−0.10% of the indicated value, whichever is greater.

As used herein, "control" is an alternative subject or sample used in an experiment for comparison purposes and included to minimize or distinguish the effect of variables other than an independent variable. A "control" can be a positive control, a negative control, or an assay or reaction control (an internal control to an assay or reaction included to confirm that the assay was functional). In some instances, the positive or negative control can also be the assay or reaction control.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

The term "treating", as used herein, can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

The term "preventing", as used herein includes preventing a disease, disorder or condition from occurring in an animal, which can be predisposed to the disease, disorder and/or condition but has not yet been diagnosed as having it.

As used herein, "mitigate" refers to reducing a particular characteristic, symptom, or other biological or physiological parameter associated with a disease or disorder.

As used herein, "biomarker" refers to any measurable molecule, including but not limited to polynucleotides and polypeptides, or compound in a subject whose presence, absolute amount, or relative amount, is indicative of some disease, condition, syndrome, disorder, symptom thereof, or state thereof.

As used herein sample, refers to any aliquot of a source (e.g. bodily fluid, soil sample, air sample, water sample, and the like) that can be examined for a molecule or organism of interest.

As used herein, "body fluid" refers to any liquid or liquid-like substance that originates in the body of a living organism. "Body fluid" includes, but is not limited to, whole blood, serum, buffy coat of blood or other blood fraction that contains substantially only the white blood cells and platelets, plasma, cerebral spinal fluid, urine, lymph, bile, acites fluid, and saliva.

As used herein, "diagnosis" refers to the identification or determination of the nature and circumstances of a disease, disorder, condition, syndrome, or symptom thereof in a subject.

As used herein, "prognose," refers to determining a prognosis for a disease, disorder, condition, syndrome, or symptom thereof.

As used herein, "prognosis" refers to a prediction or forecast of a chance of recovery, complete or partial, from a disease, disorder, condition, syndrome, or symptom thereof.

As used herein, "a target molecule" refers to any molecule, cell, virus, lipid or chemical compound that can be bound, either directly or indirectly, by a probe as described herein.

As used herein, "a characteristic of a temperature melting peak or curve" can refer to any mathematical description of the temperature melting peak or curve and includes, but is not limited to, the area under or above the curve, a correlation between a curve or another curve, the x, y coordinates of any position on the melting peak or curve, etc.

As used herein "optically active" refers to the ability of a compound or other molecule to absorb or emit a wavelength of light, such as in absorbance or luminescence (fluorescence, phosphorescence, chemiluminescence, electrochemiluminescence, etc.).

As used herein "electrochemically active" refers to the ability of a compound or other molecule to participate in an electron transfer reaction.

Discussion

Dual-probe enzyme-linked immunosorbent assay (ELISA) is the most widely used immunoassay platform owing to its high sensitivity and selectivity. Nonetheless, complex workflow, high expense, and the large sample volumes still remain as hampering factors for even more widespread adoption. Modern variations on ELISA have seen success, yet these methods still require expensive instrumentation and consumables while retaining the same basic workflow developed more than 30 years ago.

On the basis of simple workflow, scalability, rapidity, and low cost, homogeneous protein assays hold promise for quantification of an arbitrary protein in real time over a wide concentration range, long sought-after qualities in bioanalysis. These also utilize pairs of probes that exploit target-dependent proximity for signal generation. However, to avoid autofluorescence in biological samples, readout usually requires instrumentation for either time-resolved fluorescence or chemiluminescence, both being nonstandard or specialized. One successful option is to translate protein amount into a nucleic acid reporter. This technique lends itself to multiplexability and high sensitivity, since nucleic acid output sequences can encode target identities and are amplifiable.

With heterogeneous assays (e.g., enzyme linked immunosorbent assay, ELISA), surface bound probe-target complexes can be washed for near complete removal of interferences by physical separation. In contrast, homogeneous assays often exhibit indistinguishable output from signal and background components. Thus, despite their high potential in bioanalysis, homogeneous assays are plagued by suboptimal signal-to-background ratios and interferences.

With that said, described herein are thermofluorimetric assays, compositions, and devices configured to be used in the thermofluorimetric assays that can thermally resolve one or more molecules. Also described herein are thermally resolved electrochemical assays, compositions, and devices configured to be used in thermally resolved electrochemical assays that can thermally resolve one or more molecules. The methods and assays described herein can allow for protein and other molecule detection and/or quantification without having to separate the target protein or molecule from the sample. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Thermofluorimetric Assays

Figure 2:
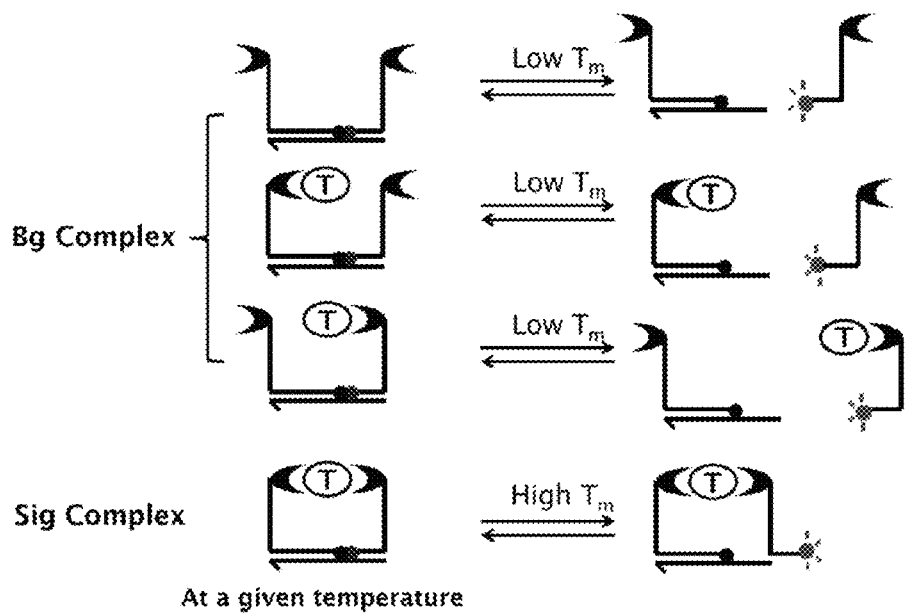
FIG. 2 shows embodiments of background (Bg) complexes and a signal (Sig) complex at a given temperature.

The thermofluorimetric assays described herein are based on the separation of complexes based on their thermodynamic properties over a thermal gradient. The general principle of the assays described herein is depicted in FIGS. 1-2. A target molecule 1000 in a sample can be bound by two probes 1010, 1020 to produce a signal complex 1030. Unbound probes and other assay molecules, such as a proximity oligonucleotide 1040, can form one or more background complexes 1050. A temperature gradient can be applied to the sample and complexes. Due to differences in the thermodynamic properties of the signal complex 1030 and the background complex 1050, the signal complex 1030 and the background complex 1050 can have different melting temperatures. As such, when a temperature gradient is applied the signal complex 1030 will generate a different thermal profile (also referred to herein as a temperature melting curve) 1060 than a background complex 1050. The signal complex 1030 can produce a first melting temperature peak 1070 and the background complex 1050 can generate a second melting temperature peak 1080. The assay can be used to detect the presence and/or quantify the amount of the target molecule in the sample.

As shown in FIG. 2, the signal complex (Sig) can have a high melting temperature ($T_m$) as compared to any background (Bg) complex that can form. The probes can be designed such that the signal complex has a predicted or known melting temperature.

The methods can contain the steps of contacting a sample with a first probe, wherein the first probe is configured to bind a target molecule, contacting the sample with a second probe, wherein the second probe is configured to bind the target molecule, forming a signal complex, thermally scanning the signal complex to form a temperature melting curve, the temperature melting curve containing a first melting temperature peak, where the first melting temperature peak corresponds to the melting temperature of the signal complex, and detecting the target molecule via measuring a characteristic of the first melting temperature peak. The methods can further comprise the step of quantifying the amount of signal complex by the peak area of the first melting temperature peak. The methods can further contain the steps of forming a background complex and wherein the temperature melting curve further comprises a second melting temperature peak, where the second temperature melting peak corresponds to the melting temperature of the background complex.

The target molecule can be proteins including protein complexes associated with biomolecules, such as metalloproteins, glycoproteins, and DNA-bound proteins, lipid rafts, carbohydrates, macrocycles, biopolymers, polyphenols, cells, or viruses. In some embodiments, the target molecule is not DNA or RNA. The first and second probes can each be independently selected from the group of an aptamer, an antibody or a fragment thereof, a protein, and an oligonucleotide.

Figure 3:
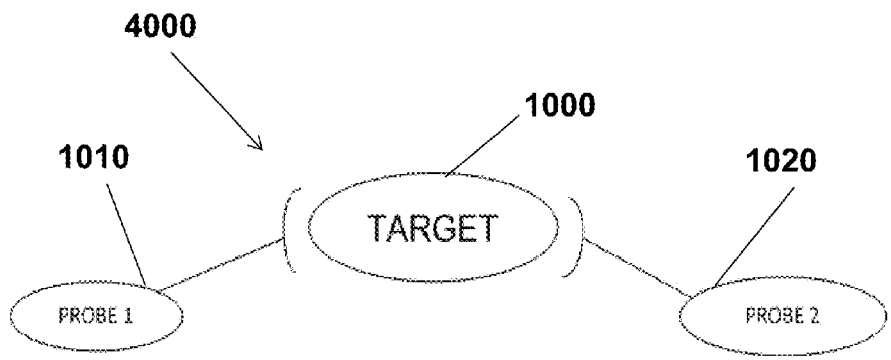
FIG. 3 shows an embodiment of a signal complex.

As shown in FIG. 3, the first 1010 and the second probe 1020 can each directly bind to the target molecule to form the signal complex 4000. Background complexes can be formed from the first probe 1010 or the second probe 1020 (but not both) binding directly to the target molecule 1000. Background complexes can also be formed by an unbound first probe or an unbound second probe or a complex in which the first probe is directly bound to the second probe.

An example of such a background complex can be a dimer formed between the first oligo probe and a second oligo probe. The first and the second probes can each independently be selected from the group of aptamers, antibodies or fragments thereof, proteins, and oligonucleotides.

In some of these embodiments, the signal complex 4000 and/or any background complex(es) can be contacted with an intercalating agent. Suitable intercalating agents (i.e. SYBR Green, L C green, Eva Green, BEBO, SYTO9, Chromofy, and various others) will be appreciated by those of skill in the art. The intercalating agent can result in a change in the complex such that a signal, such as an optical signal is produced. The step of thermally scanning the sample in these embodiments can further include the step of detecting and/or measuring a signal produced by the intercalating agent. The signal can be generated by the signal complex 4000 and/or a background complex.

In other embodiments where the signal complex 4000 is formed, the first probe 1010, the second probe 1020, or each of the first probe 1010 and the second probe 1020 can be coupled to an optically active molecule. In these embodiments, the step of thermally scanning can further contain the step of detecting and/or measuring a signal produced by the optically active molecule.

In further embodiments where the signal complex 4000*a* is formed, the first probe 1010 can be coupled to a Førster resonance energy transfer (FRET) donor molecule or a FRET acceptor molecule. The second probe 1020 can also be coupled to a FRET donor or FRET acceptor molecule so long as the first probe 1010 and the second probe 1020 are not both coupled to FRET donor or FRET acceptor. When the FRET donor and FRET acceptor are within responsive proximity to each other, such as in the signal complex 4000, FRET can occur and the FRET acceptor can produce a signal. When the FRET donor and FRET acceptor are not within responsive proximity to each other, only the FRET donor produces a signal. In these embodiments, the step of thermally scanning can further contain the step of measuring a signal produced by the FRET donor and/or FRET acceptor. Suitable FRET donors and acceptors will be appreciated by those of skill in the art. Example FRET donors are TYE665, 5-TAMRA and FAM; and example FRET acceptors are Cy5 and Blackhole quenchers.

Figure 4:
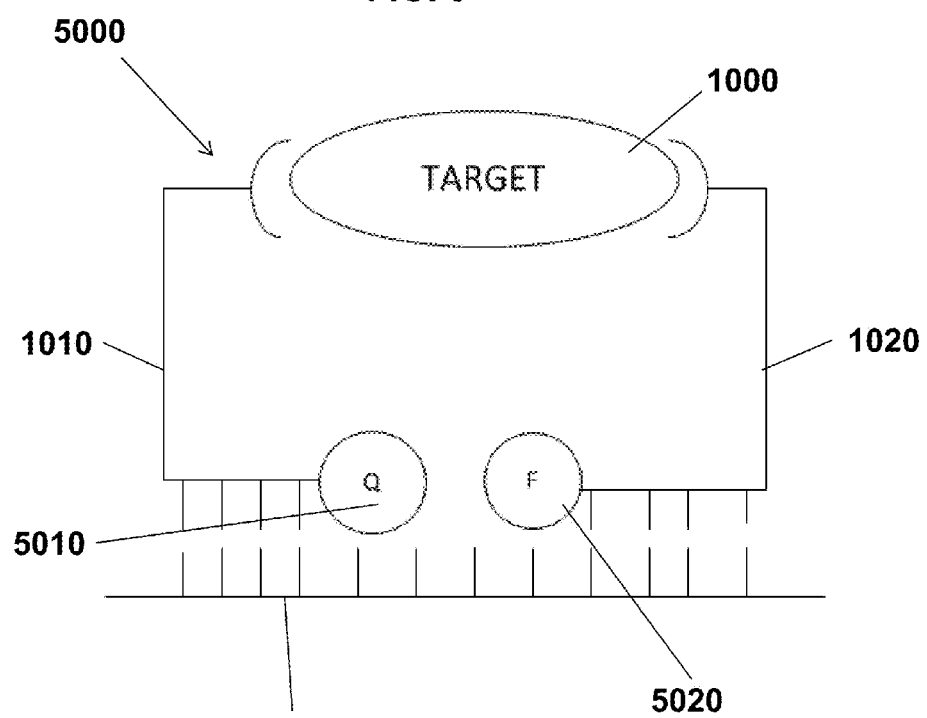
FIG. 4 shows an embodiment of a signal complex.

In further embodiments, the sample can also be contacted with a proximity oligonucleotide 1040. As shown in FIG. 4, a signal complex 5000 that includes the proximity oligonucleotide 1040 can be formed. The proximity oligonucleotide 1040 can be configured such that the first probe 1010 and the second probe 1020 can specifically bind to the proximity oligonucleotide. The first 1010 and/or the second probe(s) 1020 can be configured to specifically bind the proximity oligonucleotide 1040 as well as to the target molecule 1000. The first 1010 and the second 1020 probes can each independently be selected from the group of aptamers, antibodies or fragments thereof, proteins, and oligonucleotides. When a probe is an oligonucleotide, then specific binding can occur via hybridization. Aptamer probes can be designed to bind a specific sequence within the proximity oligonucleotide 1040. In some embodiments, the first probe and the second probe each comprise a protein binding moiety independently selected the group of aptamers, antibodies or fragments thereof, proteins, and oligonucleotides. For example, antibodies, fragments thereof, and other protein probes can be modified to contain one or more oligonucleotides that can hybridize with the proximity oligonucleotide 1040. The proximity oligonucleotide can range in size from 5 nucleotides to 100 nucleotides, with a preferred size between 8 nucleotides and 15 nucleotides. Aptamer probes can range from 5 nucleotides to 200 nucleotides, with preferred sizes between 20 nucleotides and 60 nucleotides. The proximity oligonucleotide should not have any domain to be self-reverse complemented. A pair of the proximity oligonucleotides should not be hybridized each other during thermal scanning.

In some of these embodiments where the signal complex 5000, the first probe can be configured to bind the target molecule and the proximity oligonucleotide, the second probe can be configured to bind the target molecule and the proximity oligonucleotide, and the first probe and the second probe can be said to have formed a paired bivalent probe.

As shown in FIG. 4, in some embodiments, the first probe 1010 can be coupled to a quencher molecule 5010 and the second probe 1020 can be coupled to an optically active molecule 5020. In these embodiments, the step of thermally scanning can further contain the step of measure and/or detecting a signal produced by the optically active molecule 5020.

Figure 5:
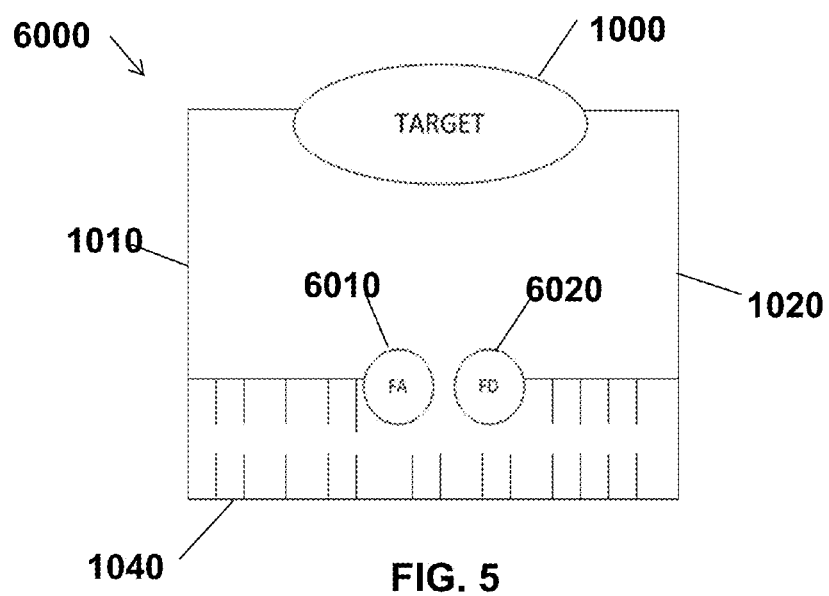
FIG. 5 shows an embodiment of signal complex.

The embodiments depicted in FIG. 5 are the same as those described in relation to FIG. 4 except that instead of a quencher molecule 5010 or an optically active molecule 5020, either the first probe 1010 or the second probe can be coupled to a FRET acceptor 6010 and the probe that is not coupled to the FRET acceptor 6020 can be coupled to a FRET donor. FRET donors and FRET acceptors are described elsewhere herein. In these embodiments, the step of thermally scanning can contain the step of measuring and/or detecting a signal generated by the FRET donor and/or FRET acceptor.

Figure 6:
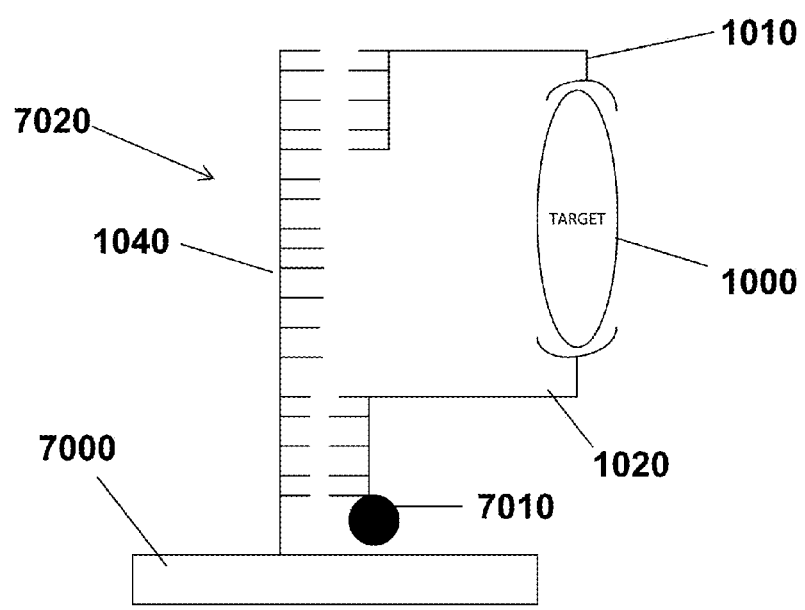
FIG. 6 shows an embodiment of a signal complex.

As shown in FIG. 6 in some embodiments that employ a proximity oligonucleotide 1040, the proximity oligonucleotide can be coupled to an electrically conductive substrate 7000. Suitable electrically conductive substrates include but are not limited to gold, platinum, graphene, graphite, activated carbon electrode, a conductive ceramic, a conductive glass, and any combination thereof. In these embodiments, the first probe 1010, the second probe 1020, or both the first 1010 and the second 1020 probes can be coupled to a redox-active molecule obvious to those skilled in the art, for example but not limited to methylene blue (MB), ferrocene/ferricinium, tris(2-2'-bipyridine)Ru(II), quinone/hydroquinone, and their derivatives, and any combination thereof. In operation when a signal complex 7020 is formed, the redox-active molecule can be in proximity to the electrically conductive substrate 7000 such that a current or a change in current is generated. In these embodiments, the step of thermally scanning can further contain the step of measuring and/or detecting the current produced by the electrically conductive substrate 7000.

Figure 7:
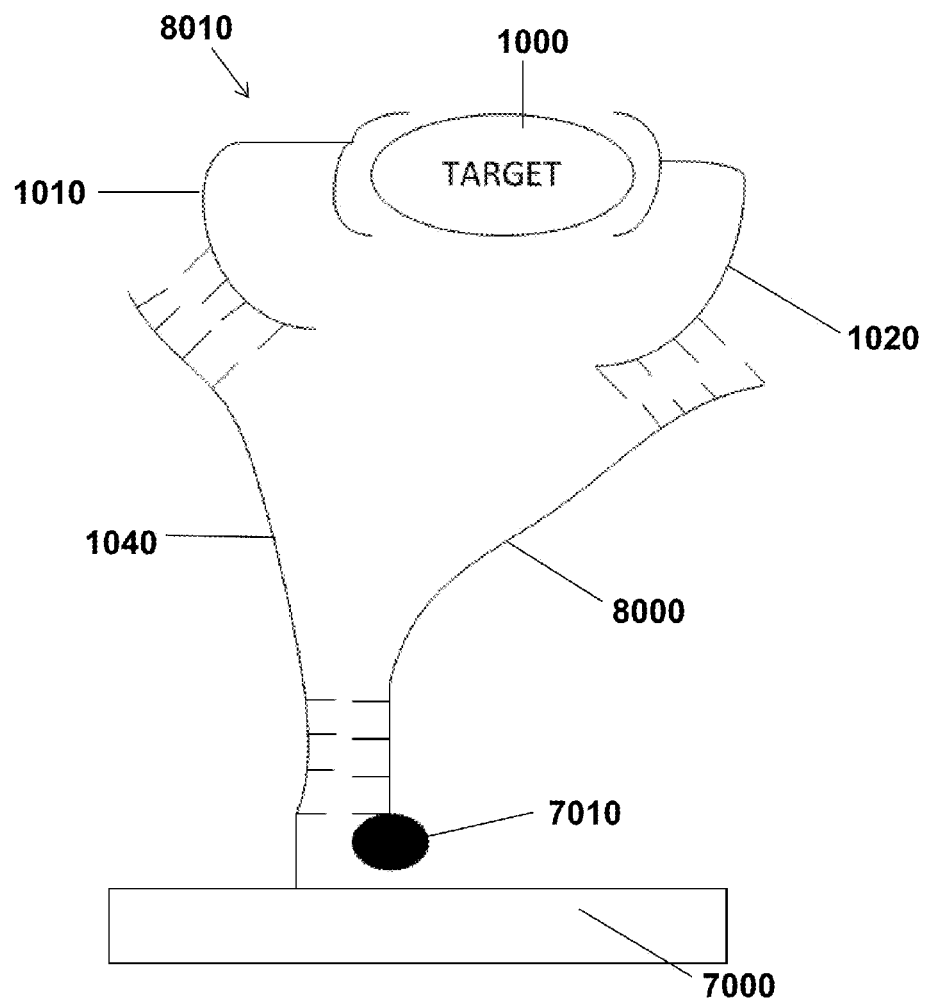
FIG. 7 shows an embodiment of a signal complex.

As shown in FIG. 7, in some embodiments that employ a proximity oligonucleotide 1040, the sample can be further contacted with a connector oligonucleotide 8000. The connector oligonucleotide 8000 can be configured to bind, such as specifically bind, to the proximity oligonucleotide 1040. In these embodiments, the second probe 1020 can be configured to bind the target molecule 1000 and the connector oligonucleotide 8000. In these embodiments, the proximity oligonucleotide 1040 can be coupled to an electrically conductive substrate 7000. In these embodiments, the first probe 1010, the second probe 1020, the connector oligonucleotide 8000, or combinations thereof, can be coupled to a redox active molecule 7010. In these embodiments, the step of thermally scanning can further contain the step of measuring and/or detecting the current produced by the electrically conductive substrate 7000.

Figure 8:
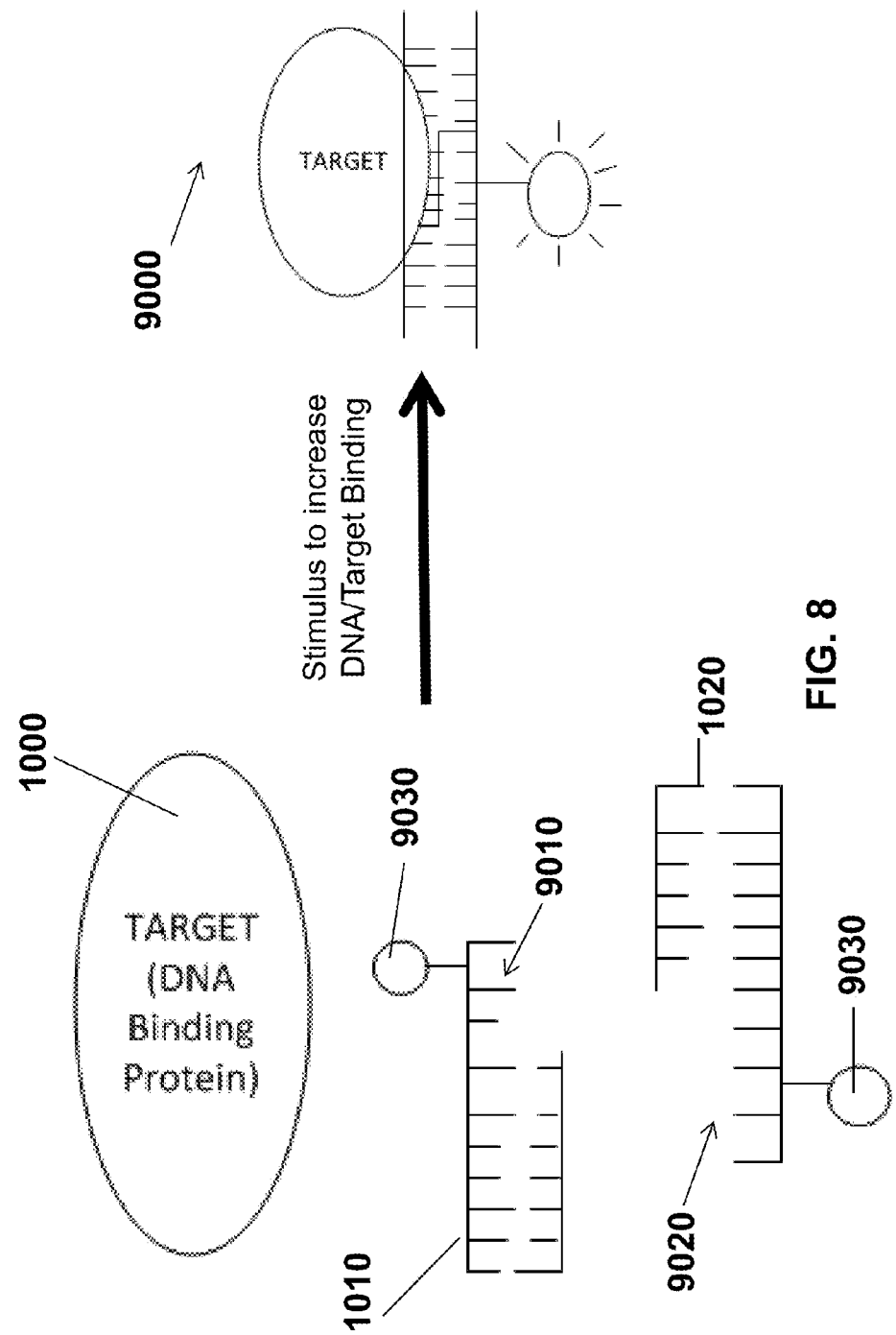
FIG. 8 shows an embodiment of formation of a signal complex and signal complex.
Figure 9:
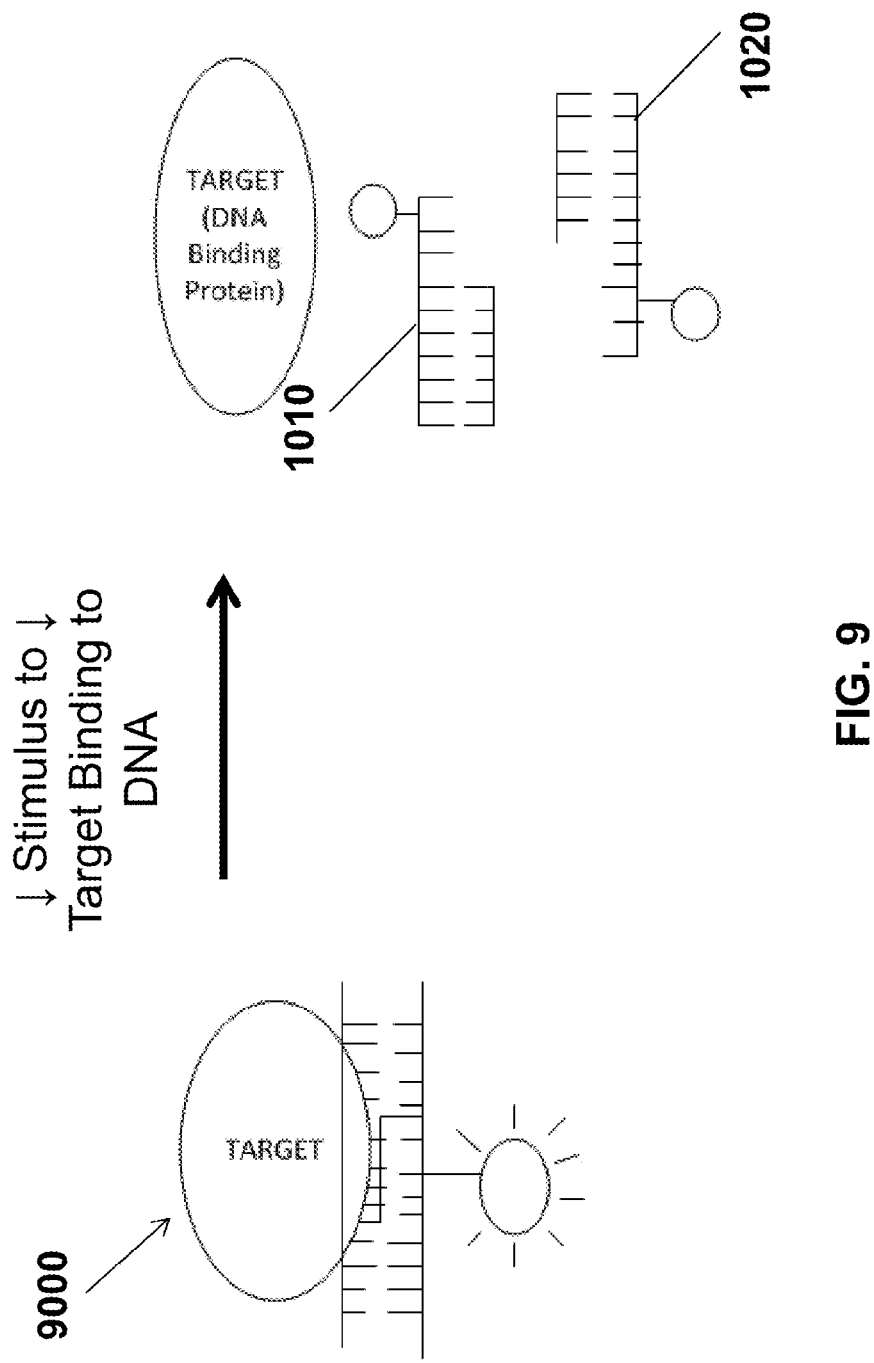
FIG. 9 shows an embodiment of formation of a signal complex and signal complex.

In some embodiments, the target molecule is a nucleotide binding target molecule. As shown in FIGS. 8 and 9, in these embodiments, the first probe and the second probe can each be an oligonucleotide that contains a single stranded overhang 9010, 9020 at one end that is complementary to the overhang of the other probe. In some embodiments, the first probe 1010 and/or the second probe 1020 can be coupled to an optically active molecule 9030 that can change in signal when the signal complex 9000 is formed. In other embodiments, the first probe 1010 can be coupled a FRET donor and the second probe 1020 can be coupled to a FRET acceptor. In yet further embodiments, the first probe 1010 can be coupled to a quencher molecule and the second probe can be coupled to an optically active molecule. When the signal complex 9000 is formed in some of these embodiments, the target molecule 1000 is bound to both the first 1010 and the second probes 1020 such that the overhang ends of both the first and the second probes come in and stay bound to each other so long as the target molecule is bound to the probes. A signal complex can be formed (FIG. 8) or disassociated (FIG. 9) when the target molecule is exposed to a stimulus that causes the target molecule to bind to the oligonucleotide probes (FIG. 8) or unbind (FIG. 9 the oligonucleotide probes. These embodiments can include the step of measuring and/or detecting a signal from a FRET donor, a FRET acceptor, or an optically active molecule.

In some embodiments no proximity nucleotide is used and the first and the second probes can be oligonucleotides. In these embodiments, either the first or the second probe can be coupled to an electrically conductive substrate. In these embodiments, the first probe, the second probe, or each of the first probe and the second probe can be coupled to a redox-active molecule. In these embodiments, the step of thermally scanning can further contain the step of measuring the current produced by the electrically conductive substrate.

In some of the embodiments described herein, the characteristic of the first melting temperature peak can be compared to a predetermined value for the characteristic of the first melting temperature peak. In some of the embodiments described herein, the characteristic of the first melting temperature peak can be compared to a predetermined value for the characteristic of the first melting temperature peak. In some of these embodiments, the characteristic of the second melting temperature peak can be compared to a predetermined value for the characteristic of the second melting temperature peak. In others, the characteristic of the second melting temperature peak can be compared to a predetermined value for the characteristic of the second melting temperature peak.

Figure 19:
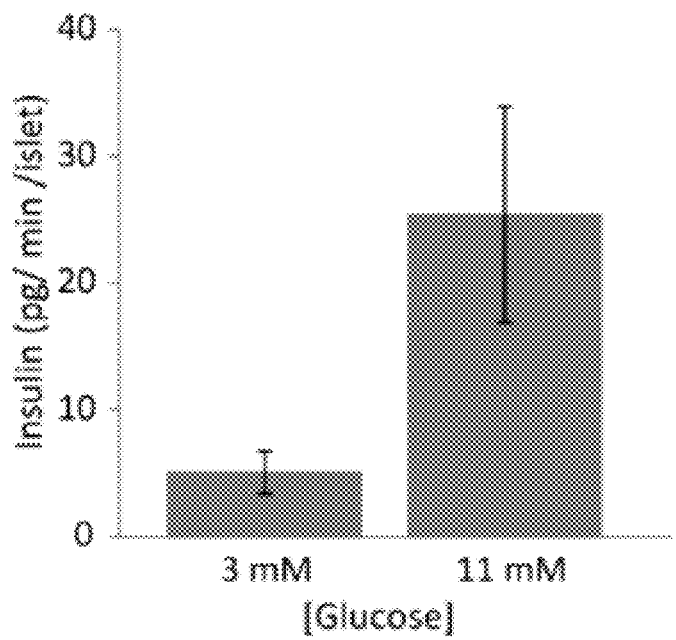
FIG. 19 shows a graph demonstrating insulin TFAB in cell media. 1 h of insulin secretion is directly quantified from only 7 murine pancreatic islets at low and high glucose.

In some embodiments described herein the melting temperature of the signal complex can be predetermined based on the calculated melting temperature of background complex specified by base pairing with connector oligonucleotide. This can be accomplished by developing an appropriate model for the system in question, such as the model shown in FIGS. 19 and 29.

Thermally Controlled Assay Systems

Figure 10:
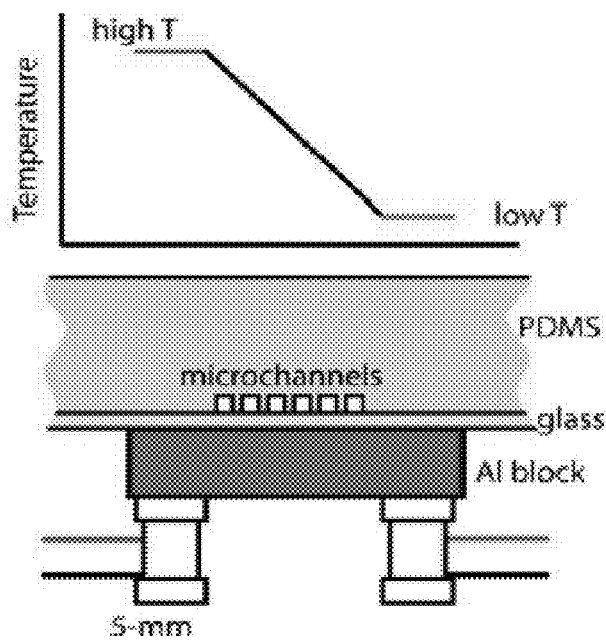
FIG. 10 shows an embodiment of a gradient microfluidic device configured to perform a thermally resolved assay.
Figure 11:
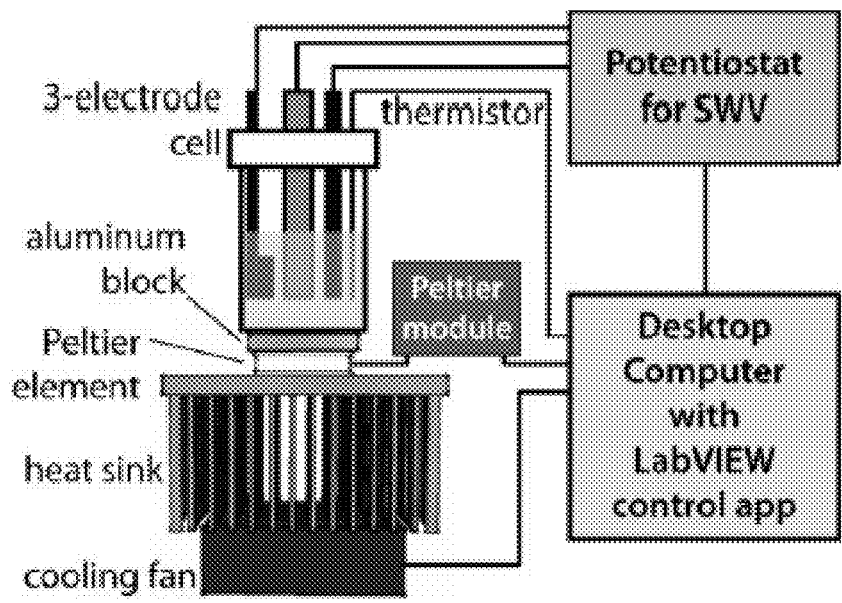
FIG. 11 shows an embodiment of a thermally controlled electrochemical cell to perform a thermally resolved assay.

FIGS. 10-11 show embodiments of a system that can be used to perform at least part of any method described herein. One embodiment of a gradient microfluidic TFAB system is shown in FIG. 10. Miniature Peltier elements (5-mm) can be used to create a thermal gradient along an aluminum block, which can be translated through a thin glass coverslip floor to an aqueous solution that can be contained within one or more microfluidic channels. The microfluidic devices can be fabricated in polydimethylsiloxane (PDMS), which is thermally insulating. Other thermally insulating materials can be used and will be appreciated by those of skill in the art. Insulating material (not shown in figure) can also be added surrounding the Peltier elements and/or the metal block. To rapidly evaluate the thermal gradient integrity, a thermal imaging camera (FLIR E50bx MSX) with sub-millimeter image resolution can be employed. This can allow empirical optimization in real-time, compared to more time-consuming and possibly inaccurate thermal simulations. The temperature resolution of this system can be defined by the number of channels packed into the thermal gradient. With a gradient from 10-60° C., over a distance of 20 mm and a resolution of 0.5° C., at least 100 microfluidic channels of 100 μm width and 100 μm spacing can be included in the system. Samples can be introduced in parallel into all channels, and fabrication can be accomplished using photolithography. A standard fluorescence microscope can be used for imaging and image analysis can be accomplished using ImageJ or other suitable image capture and analysis software.

Another embodiment of a thermally controlled electrochemical system is shown in FIG. 11. The system can contain a regulator can be configured to control the temperature of the electrochemical cell between about 10 to about 80° C. The system can contain a potentiostat that can be coupled to an electrode cell. The electrode cell can be coupled to an aluminum block. The potentiostat can be coupled or in communication with to a computer. The system can be designed with an integrated Peltier control module, capable of delivering 2.2 A at up to 5 V. A 30 mm×30 mm Peltier unit capable of sustaining a 66° C. temperature difference can be used for the thermal pumping, and a thermistor can be used to obtain temperature measurements. The regulator can contain a Peltier module that can be coupled to a Peltier element and aluminum block. The Peltier module can also be coupled to or in communication with the computer. The computer can contain processing logic to control the system. On the opposing side of the Peltier module the device can contain a heat sink. The heat sink can contain cooling fins and an electric fan. In some embodiments the electric fan can produce airflow of about 3.7 ft$^3$ min$^{-1}$. The system can contain a controller that can be driven with a processing logic, such as a LabView or other suitable application. The processing logic can integrate safety shutdown procedures, digital proportional-integral-derivative (PID) control, and/or data capture and/or storage functionalities. The processing logic can be interfaced with a potentiostat that is coupled to the system and can be configured to trigger voltammetric scanning after the electrochemical cell is thermally equilibrated at each set measurement temperature.

Uses of Thermally Resolved Assays and Systems

The thermofluorimetric and thermally controlled electrochemical assays and systems described herein can be used to detect and/or quantify one or more target proteins. The thermofluorimetric and thermally controlled electrochemical assays and systems described herein can be used in a clinical or veterinary setting to aid in diagnosing and/or treating a human or animal patient. The thermofluorimetric and thermally controlled electrochemical assays and systems described herein can be used in research and allow for high-throughput, sensitive, and low cost analysis of target molecules with in a sample. The thermofluorimetric and thermally controlled electrochemical assays and systems described herein can be used in sensors and the like to monitor an environment, such as the air or a water source for contaminants.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Introduction:

Dual-probe enzyme-linked immunosorbent assay (ELISA) is the most widely used immunoassay platform owing to its high sensitivity and selectivity. Nonetheless, complex workflow, high expense, and the large sample volumes still remain as hampering factors for even more widespread adoption. Modern variations on ELISA have seen success, yet these methods still require expensive instrumentation and consumables while retaining the same basic workflow developed more than 30 years ago.

On the basis of simple workflow, scalability, rapidity, and low cost, homogeneous protein assays hold promise for quantification of an arbitrary protein in real time over a wide concentration range, long sought-after qualities in bioanalysis. These also utilize pairs of probes that exploit target-dependent proximity for signal generation. However, to avoid autofluorescence in biological samples, readout usually requires instrumentation for either time-resolved fluorescence or chemiluminescence, both being nonstandard or specialized. One successful option is to translate protein amount into a nucleic acid reporter. This technique lends itself to multiplexability and high sensitivity, since nucleic acid output sequences can encode target identities and are amplifiable.

With heterogeneous assays (e.g., enzyme linked immunosorbent assay, ELISA), surface bound probe-target complexes can be washed for near complete removal of interferences by physical separation. In contrast, homogeneous assays often exhibit indistinguishable output from signal and background components. Thus, despite their high potential in bioanalysis, homogeneous assays are plagued by suboptimal signal-to-background ratios and interferences. Herein, we introduce an analytical tool that exploits thermofluorimetric analysis of bivalent probes (TFAB) for robust yet facile protein quantification. First, high signal is ensured by sample incubation with bivalent probes at low temperature, without regard for nonspecific background. A qPCR instrument, with capability to thermally scan samples during fluorescence readout, is leveraged to efficiently distinguish between protein-bound and unbound probes, without physical separation. Quantitative and multiplexed protein detection is demonstrated with TFAB; the method is shown to be functional in human serum, human plasma, and cell secretion samples and is miniaturized to the picoliter scale. On the basis of its success with bivalent antibody-oligonucleotide and aptamer probes, it is expected that this TFAB methodology will be generally applicable for mix-and-read assays of a variety of protein analytes in the future.

Material and Methods:

Reagents and Materials: All solutions were prepared with deionized, ultra-filtered water (Fisher Scientific). The following reagents were used as received: insulin antibodies (clones 3A6 and 8E2; Fitzgerald Industries), bovine serum albumin (BSA), human thrombin and human insulin (Sigma-Aldrich), Uracil-DNA excision mixture (Epicentre), Amplitaq Gold DNA polymerase (Life Technologies), T4 DNA ligase (New England BioLab Inc.). Oligonucleotides were obtained from Integrated DNA Technologies (IDT; Coralville, Iowa), with purity and yield confirmed by mass spectrometry and HPLC, respectively. All DNA sequences used are given in FIG. 24; modifications included carboxytetramethylrhodamine (5-TAMRA; $\lambda max=546$ nm; $\lambda em=579$ nm), TYE665 ($\lambda max=645$ nm; $\lambda em=665$ nm), Blackhole Quencher-1 (BHQ1; $\lambda max=534$ nm), and Blackhole Quencher-2 (BHQ2; $\lambda max=578$ nm). DNA sequences were designed and optimized computationally using the nucleic acid package web server (NUPACK) (J. N. Zadeh, C. D. Steenberg, J. S. Bois, B. R. Wolfe, M. B. Pierce, A. R. Khan, R. M. Dirks, N. A. Pierce, *Journal of computational chemistry* 2011, 32, 170-173.) Pathogen screened normal human serum and plasma samples were purchased from Bioreclamation. The assay buffer consisted of 50 mM Tris-HCl at pH 7.5, 100 mM NaCl, 1 mM MgCl2, and 1% BSA.

Preparation of probes. Thrombin aptamers (Thr1_BHQ1 and Thr2_TAMRA) were prepared by heating to 94° C. for 7 min, followed by rapid cooling on ice for 5 min in assay buffer. Antibody-oligonucleotide conjugates were prepared as described previously (C. J. DeJournette, J. Kim, H. Medlen, X. Li, L. J. Vincent, C. J. Easley, *Analytical chemistry* 2013, 85, 10556-10564) by covalent attachment of AbA_BHQ1 to insulin antibody 3A6 (probe: 3A6_BHQ1) and AbB_TYE665 to insulin antibody 8E2 (probe: 8E2_TYE665), respectively. Conjugation and purification were accomplished using the Antibody-Oligonucleotide All-In-One Conjugation Kit (Solulink), according to the manufacturer's instructions. The final conjugate concentrations were determined via the BCA protein assay.

Thermofluorimetric analysis of bivalent probes (TFAB): For thrombin TFAB, the concentration of each component in a total of 20 microliter assay buffer was as follows: 50 nM each of the pair of thrombin aptamers and 70 nM of DNA connector. For insulin TFAB in 20 microliter assay buffer, concentrations were as follows: 6.3 nM each of the pair of insulin antibody-oligonucleotide conjugates and 18.9 nM of DNA connector. 5 microliter of sample was used in both TFABs. The assay mixture was prepared at room temperature and stored at 4° C. until its use. After incubation of samples with assay mixture at 37° C. for 15 min, the mixture was incubated either at 4° C. for additional 10 min for the full range of thermal scan (4° C.-65° C.) or at 22° C. for additional 5 min for the short range of thermal scan (20° C.-55° C.) before thermofluorimetric analysis. Fluorescence emission, either from TAMRA (590±20 nm) for thrombin TFAB or TYE665 (650±40 nm) for insulin TFAB, was measured after reaching each targeted temperature. Isothermal fluorescence proximity assays (FPA) were performed at 22° C.

Thermofluorimetric data analysis: Raw fluorescence emission data versus temperature was first corrected by subtracting data from a blank solution (assay buffer only) then normalized by the maximum, unquenched fluorescent probe (labeled DNA strands only, without quencher) over the entire temperature range. Derivative (dF/dT) plots were obtained using a first-derivative Savitzky-Golay filter in Microsoft Excel over a moving 5-point window. For quantitative analysis, dF/dT peaks (signal and background) were processed by nonlinear least squares fitting to the sum of two Gaussian peaks (Microsoft Excel, Solver add-in), with fixed mean peak temperatures defined by pilot experiments. These deconvoluted peak areas were referred to as "background melt peak area" (lower Tm) and "signal melt peak area" (higher Tm).

Figure 26:
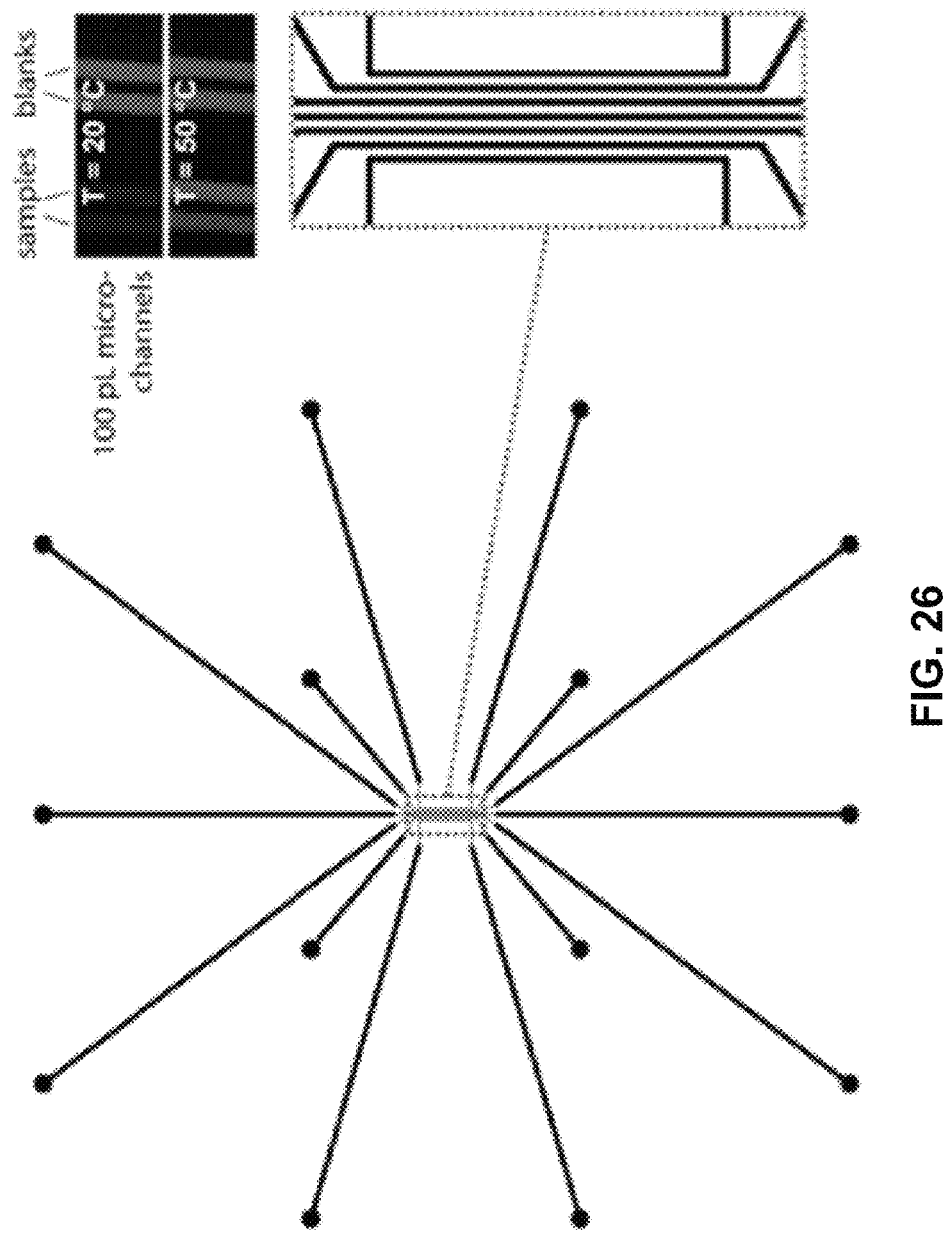
FIG. 26 shows a cartoon of the photomask design. A seven-channel microfluidic device was designed specifically for small-volume fluorescence imaging (100 pL per channel in imaging region). Seven parallel channels, each 20 micrometers in width and 16 micrometers in depth at the imaging region (zoomed inset), were fabricated in polydimethylsiloxane (PDMS) using soft lithography. Fluorescence emission (620±30 nm) from microchannels was imaged with a Nikon Ti-E wide-field inverted fluorescence microscope with a 40× objective lens and an interrogated volume of 100 pL in each microchannel.
Figure 27:
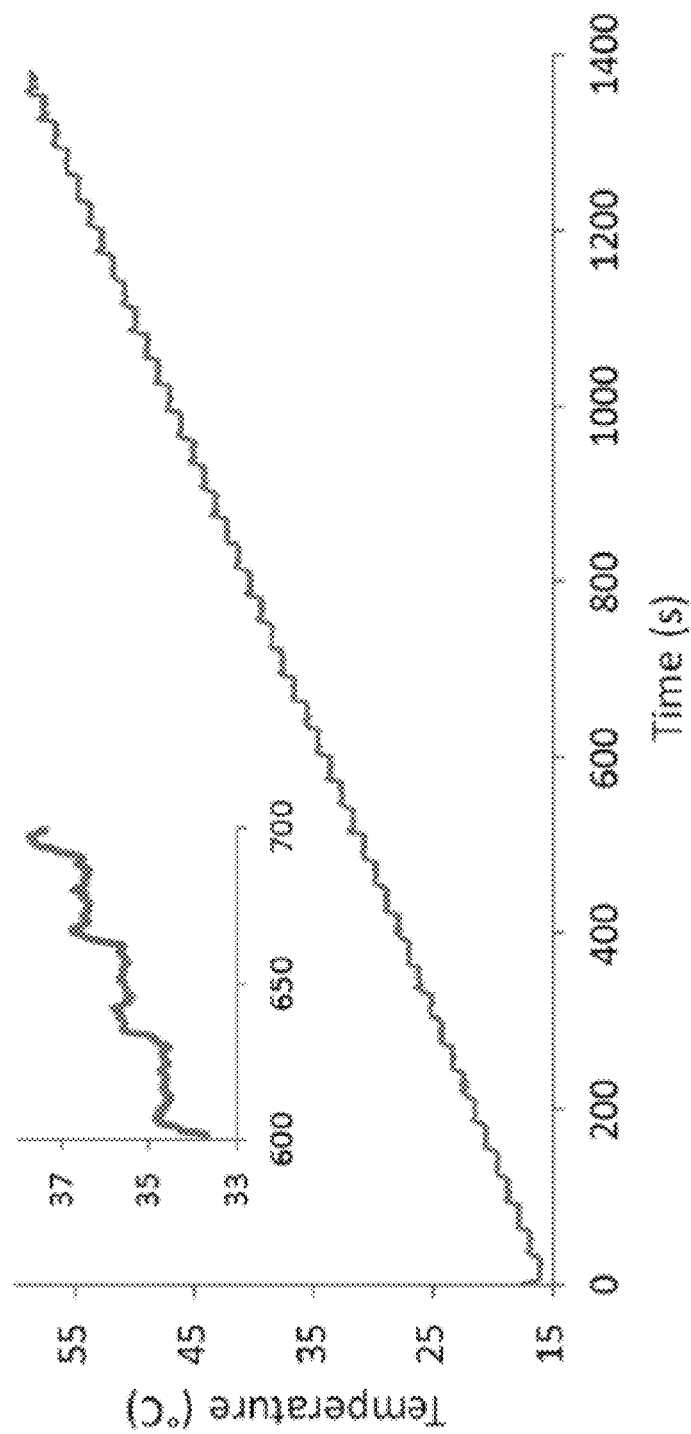
FIG. 27 shows a graph and inset demonstrating characterization of the temperature control system during a typical run of microchip TFAB.

Microfluidic TFAB: The system was designed utilizing a Maxim Integrated MAX1978 integrated controller for peltier modules, capable of delivering 2.2 A at up to 5 V. One 30×30 mm CP30138 peltier module (CUI Inc.), capable of sustaining a 66° C. temperature difference, was used to for the thermal pumping. The hot side of the peltier module was fitted with a 40 mm×40 mm×23 mm heat sink and a 30 mm×30 mm fan capable of 3.72 ft3 min-1 of airflow. Seven parallel microfluidic channels, each 20 micrometers in width and 16 micrometers in depth, were fabricated in polydimethylsiloxane (PDMS) using soft lithography. The photomask design is given in FIG. 26. Fluorescence emission (620±30 nm) from micro channels was imaged with a Nikon Ti-E wide-field inverted fluorescence microscope with a 40× objective lens and an interrogated volume of 100 pL in each microchannel. The temperature of the micro channels was increased from 15° C. to 60° C. in 1.0° C. increments, with 30 s hold times before fluorescence emission measurement (average of 2.0° C. min-1). This temperature scanning was accomplished using an in-house built controller with a Peltier element driven by proportional-integral-derivative control (PID) provided by a LabVIEW application written in-house. The program integrates safety shutdown procedures, proportional integral derivative control, and data capture functionality. Thermal record data is shown in FIG. 27. As shown in the inset data of FIG. 27, once stabilized at the set temperature, the control system typically held the microfluidic device to within <0.2° C. of the set point. The temperature of the micro channels was increased from 15° C. to 60° C. in 1.0° C. increments, with 30 s hold times before fluorescence emission measurement (average of 2.0° C. min-1).

Figure 13:
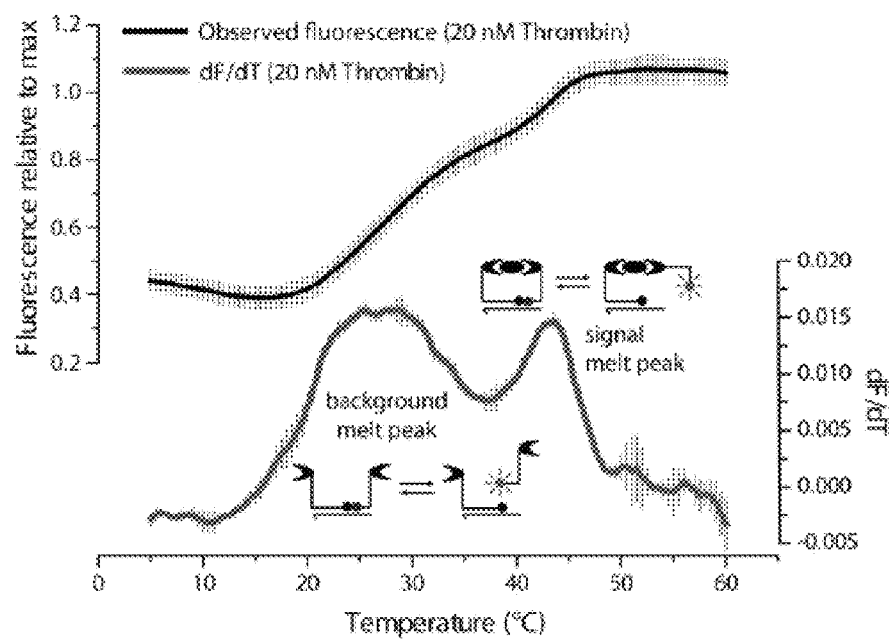
FIG. 13 shows a graph demonstrating fluorescence (F) and the derivative of fluorescence (dF/dT) in the presence of 20 nM thrombin during thermal scanning.
Figures 14A, 14B, 14C:
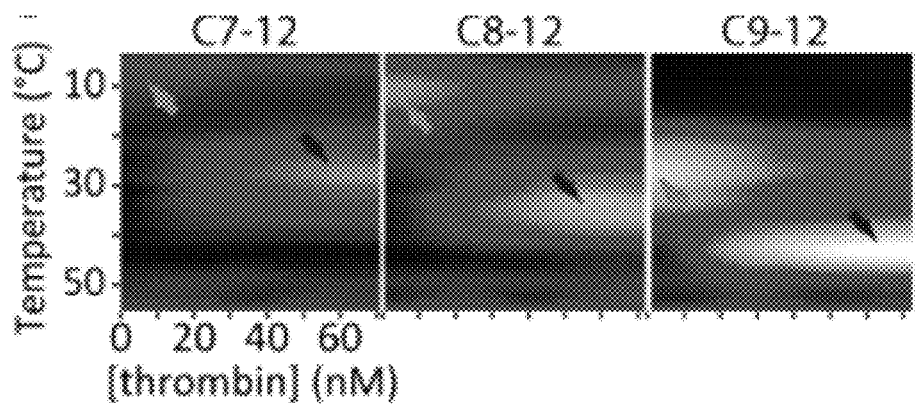
FIGS. 14A-14C show heat maps for thrombin TFABs using C7-12 (FIG. 14A), C8-12 (FIG. 14B), or C9-12 (FIG. 14C) length connectors.

Results: To enable readout of protein levels using DNA-based probe assemblies, target-driven probe proximity (referred to herein as "signal") is assessed by quantifying the hybridization of oligonucleotide tails present on a paired bivalent probe at equilibrium. Target-independent DNA annealing (referred to as "background") will be inevitable at equilibrium and will be indistinguishable from signal via isothermal readout. FIG. 12 shows a schematic of signal and background complexes in TFAB, where complex assembly promotes fluorescence quenching. Rather than minimizing background, as in optimization studies of isothermal assays, a key aspect of TFAB is that both complexes (signal and background) are further stabilized by a longer DNA connector. This creates a noncovalent assembly that can serve as a bivalent probe, an advantage since multivalency is known to impart significantly higher affinity toward protein analytes through entropic stabilization. As shown in FIG. 13, thermofluorimetric analysis enables facile analytical separation of signal and background complexes in a homogeneous manner. It is noteworthy that there is a strong signal peak with 20 nM thrombin, even though the $K_d$ values of the aptamers are higher at 26 and 128 nM, an effect of the enhanced stability of the bivalent probes.

Since enthalpy-driven DNA hybridization is more temperature sensitive, DNA connectors were customized for tunable complex stability, as shown in heat maps in FIGS. 14A-C and 15A-C. The protein-dependent "proximity effect" is clearly observed in these dF/dT maps, with signal peaks located diagonally down and to the right compared to background. Even without exhaustive studies of complex formation, it is clear that these maps should be excellent tools for optimizing conditions of many DNA-driven proximity assays. For example, with the isothermal fluorescence proximity assay for thrombin detection at room temperature, C8-12 can be chosen as the optimal connector length, since background complexes are unstable yet signal complexes are stable at this temperature FIG. 14B. With protein-dependent signal peaks clearly distinguishable from background peaks, we next demonstrate that signal peak area and height are proportional to protein quantity. The heat maps in FIGS. 14A-C and 15A-C show this effect clearly with increased intensity with protein concentration. Through non-linear least-squares fitting of the data to a sum of two Gaussian peaks, it was possible to deconvolute contributions of background and signal complexes. This post processing made it possible to extract true, protein-driven signal from total output and to essentially reduce background contributions to zero. In FIG. 16, deconvoluted signal melt transition (SMT) areas are plotted as a function of thrombin concentration in buffer. To confirm protein and probe stability during TFAB, the temperature was repeatedly scanned above and below the signal melting transition.

Figure 17:
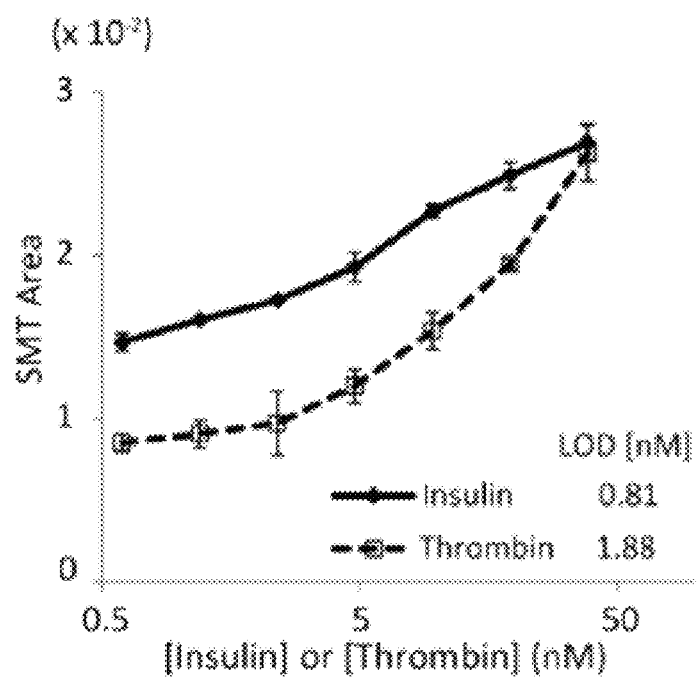
FIG. 17 shows a graph demonstrating duplex TFAB for insulin and thrombin quantification in 10-fold diluted human serum.
Figure 18:
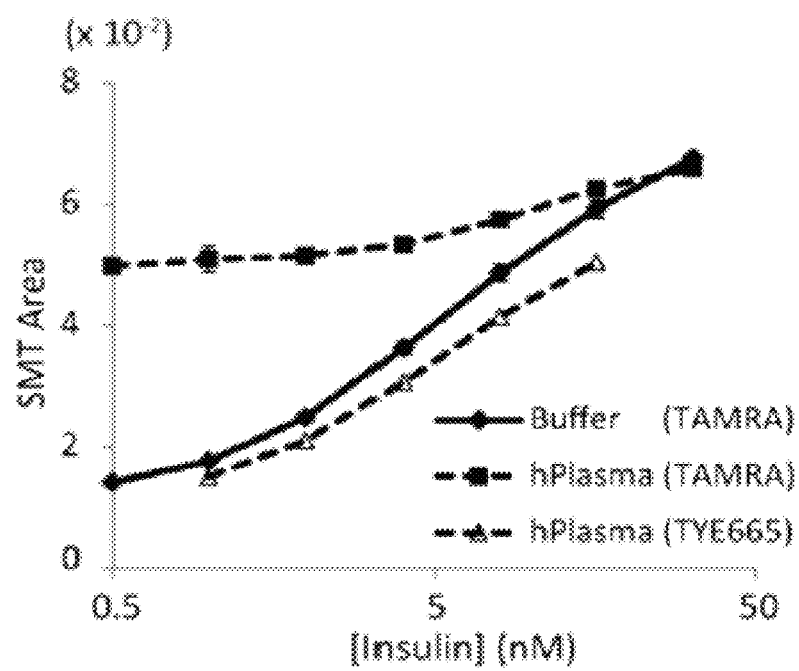
FIG. 18 shows a graph demonstrating insulin TFAB in 10-fold diluted human plasma (filtered); longer wavelength fluorescence emission (TYE66S) was shown to reduce autofluorescence effects as well.
Figure 28:
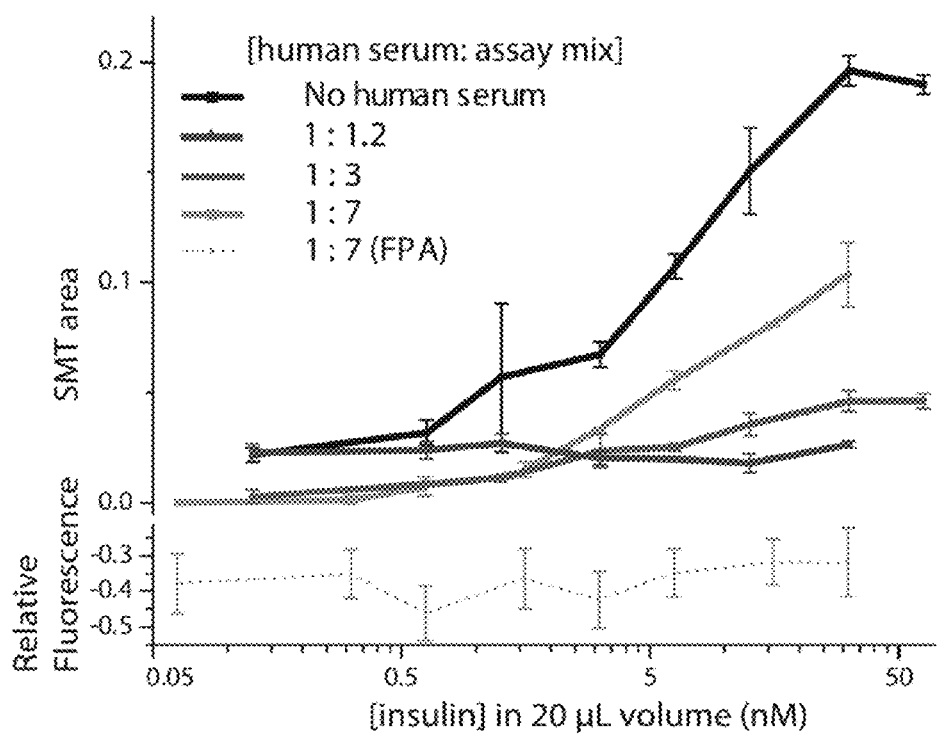
FIG. 28 shows a graph demonstrating matrix effects on TFAB and isothermal fluorescence proximity assay (FPA). Insulin was spiked in samples containing various amount of human serum. The lower plot shows that FPA is ineffective in complex matrices. Using the same exact optical system, TFAB is able to quantify insulin in the same sample due to the elimination of background fluorescence through thermal scanning and peak separation.
Figure 29:
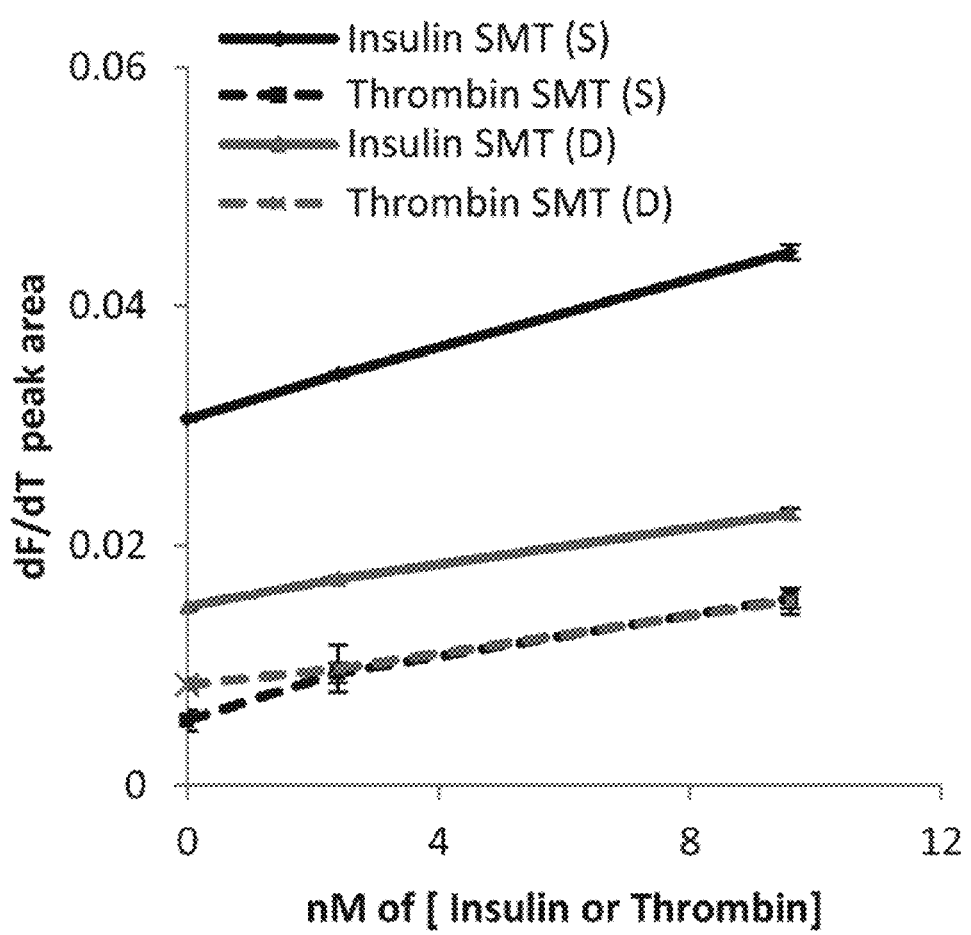
FIG. 29 shows a graph demonstrating singleplex and duplex TFABs in 10-fold diluted serum samples for thrombin and insulin detection. The values in y-intercept are lower in thrombin assays, presumably due to well-separated background and signal melt peaks. The slopes representing assay sensitivity are slightly higher in duplex assay in both insulin and thrombin detection.

The data shows that assay sensitivity was maintained through at least five scans. Slight increases in the limit of detection (LOD) suggest mild thermal degradation, but these effects were minimal. Notably, the LOD in scan 1 was subnanomolar, at 0.42 nM. Since it relies merely on direct fluorescence readout in solution (without any immobilized materials like beads), the assay also shows superior scalability through successful assaying of only 1 amol of thrombin in 100 pL micro channels (FIG. 16 inset). TFAB was then proven functional for direct fluorescence readout in 10-fold diluted human serum (FIG. 17), while isothermal versions of the same assay are nonresponsive in serum due to autofluorescence interferences (FIG. 28). TFAB is capable of analytically separating signal melt transitions from slowly varying autofluorescence background. Control over DNA connector sequences also allows multiplexed protein detection; insulin and thrombin were simultaneously quantified in serum with LODs of 0.81 and 1.88 nM (FIG. 17), without compromising performance from the respective singleplex assay (FIG. 29). The assay is functional in even more complex human plasma samples, where near complete recovery of sensitivity is possible using a red fluorescent tag (FIG. 18). Finally, it is demonstrated that TFAB is useful for hormone secretion quantification from murine pancreatic islets in cell media (FIG. 19), where release of insulin is quantified from only 7 islets under physiologically relevant glucose concentrations. This application could find use in screening of islet function for transplantation or more generally for drug screening applications with various cell types.

Example 2

Figure 24:
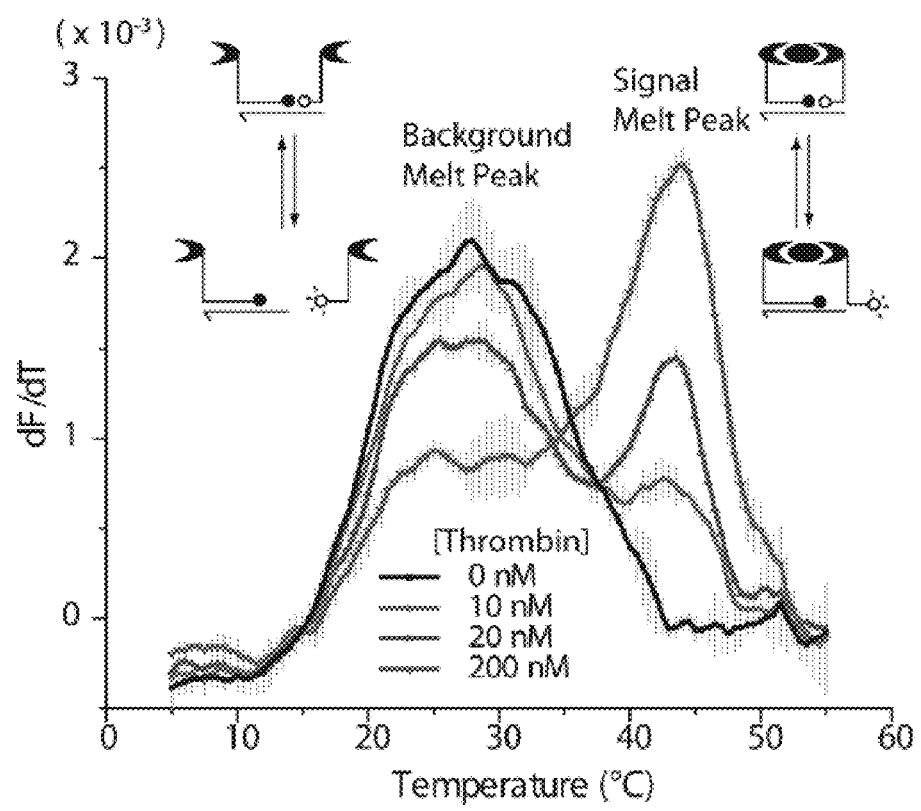
FIG. 24 shows a graph demonstrating Thrombin-dependent change in peak areas of background melt transition (BMT) and of signal melt transition (SMT).

TFAB was performed to detect varying concentrations of thrombin. The results are demonstrated in FIG. 24. A pair of thrombin aptamer probes containing each proximity oligonucleotide and a connector oligonucleotide were added to the sample containing thrombin and incubated for 15 min at 37° C. After incubation, the mixture was incubated at 4° C. for additional 10 min for the full range of thermal scan (4° C.-65° C.). The fluorescence emission was measured after reaching each targeted temperature. The concentration of each probe in a total of 20 microliters of assay buffer was as follows: 50 nM each of the pair of thrombin aptamers and 70 nM of connector oligonucleotide. As temperature increased, the fluorescence signal was also increased due to the dissociation of the background and signal complexes. FIG. 24 represents the first derivative of fluorescence signal over temperature was plotted with temperature.

Materials and Methods:

Thrombin aptamers (Thr1_BHQ1 and Thr2_TAMRA) were prepared by heating to 94° C. for 7 min, followed by rapid cooling on ice for 5 min in assay buffer. For thrombin TFAB, the concentration of each component in a total of 20 microliter assay buffer was as follows: 50 nM each of the pair of thrombin aptamers and 70 nM of DNA connector. For thrombin TFAB, the concentration of each component in a total of 20 microliter assay buffer was as follows: 50 nM each of the pair of thrombin aptamers and 70 nM of DNA connector. The assay mixture was prepared at room temperature and stored at 4° C. until its use. After incubation of samples with assay mixture at 37° C. for 15 min, the mixture was incubated either at 4° C. for additional 10 min for the full range of thermal scan (4° C.-65° C.) or at 22° C. for additional 5 min for the short range of thermal scan (20° C.-55° C.) before thermofluorimetric analysis. Fluorescence emission from TAMRA (590±20 nm) for thrombin TFAB was measured after reaching each targeted temperature. Isothermal fluorescence proximity assays (FPA) were performed at 22° C.

For data analysis, raw fluorescence emission data versus temperature was first corrected by subtracting data from a blank solution (assay buffer only) then normalized by the maximum, unquenched fluorescent probe (labeled DNA strands only, without quencher) over the entire temperature range. Derivative (dF/dT) plots were obtained using a first-derivative Savitzky-Golay filter in Microsoft Excel over a moving 5-point window. For quantitative analysis, dF/dT peaks (signal and background) were processed by nonlinear least squares fitting to the sum of two Gaussian peaks (Microsoft Excel, Solver add-in), with fixed mean peak temperatures defined by pilot experiments. These deconvoluted peak areas were referred to as "background melt peak area" (lower Tm) and "signal melt peak area" (higher Tm).

Example 3

A duplex TFAB to detect Insulin and Thrombin was performed. The results are shown in FIG. 17. A procedure to perform a duplex TFAB was the same as that for singleplex TFAB described in example 2. Probe pairs and a connector oligonucleotide to detect Insulin and those to detect Thrombin were mixed and subsequently used for the simultaneous detection of Insulin and Thrombin in a sample. Different melting temperatures between insulin-containing and thrombin-containing signal complexes allowed the corresponding signal peaks being separated with a single fluorescence detection channel during thermal scanning Materials and Methods.

Thrombin aptamers (Thr1_BHQ1 and Thr2_TAMRA) were prepared by heating to 94° C. for 7 min, followed by rapid cooling on ice for 5 min in assay buffer. Antibody-oligonucleotide conjugates were prepared as described previously (C. J. DeJournette, J. Kim, H. Medlen, X. Li, L. J. Vincent, C. J. Easley, *Analytical chemistry* 2013, 85, 10556-10564) by covalent attachment of AbA_BHQ1 to insulin antibody 3A6 (probe: 3A6_BHQ1) and AbB_TYE665 to insulin antibody 8E2 (probe: 8E2_TYE665), respectively. Conjugation and purification were accomplished using the Antibody-Oligonucleotide All-In-One Conjugation Kit (Solulink), according to the manufacturer's instructions. The final conjugate concentrations were determined via the BCA protein assay.

Thermofluorimetric analysis of bivalent probes (TFAB): For thrombin TFAB, the concentration of each component in a total of 20 microliter assay buffer was as follows: 50 nM each of the pair of thrombin aptamers and 70 nM of DNA connector. For insulin TFAB in 20 microliter assay buffer, concentrations were as follows: 6.3 nM each of the pair of insulin antibody-oligonucleotide conjugates and 18.9 nM of DNA connector. 5 microliter of sample was used in both TFABs. The assay mixture was prepared at room temperature and stored at 4° C. until its use. After incubation of samples with assay mixture at 37° C. for 15 min, the mixture was incubated either at 4° C. for additional 10 min for the full range of thermal scan (4° C.-65° C.) or at 22° C. for additional 5 min for the short range of thermal scan (20° C.-55° C.) before thermofluorimetric analysis. Fluorescence emission, either from TAMRA (590±20 nm) for thrombin TFAB or TYE665 (650±40 nm) for insulin TFAB, was measured after reaching each targeted temperature. Isothermal fluorescence proximity assays (FPA) were performed at 22° C.

Thermofluorimetric data analysis: Raw fluorescence emission data versus temperature was first corrected by subtracting data from a blank solution (assay buffer only) then normalized by the maximum, unquenched fluorescent probe (labeled DNA strands only, without quencher) over the entire temperature range. Derivative (dF/dT) plots were obtained using a first-derivative Savitzky-Golay filter in Microsoft Excel over a moving 5-point window. For quantitative analysis, dF/dT peaks (signal and background) were processed by nonlinear least squares fitting to the sum of two Gaussian peaks (Microsoft Excel, Solver add-in), with fixed mean peak temperatures defined by pilot experiments. These deconvoluted peak areas were referred to as "background melt peak area" (lower Tm) and "signal melt peak area" (higher Tm).

Example 4

Figure 20:
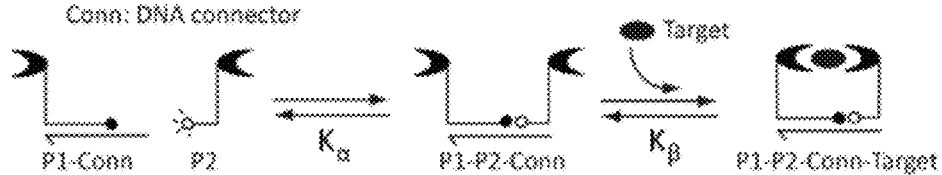
FIG. 20 shows a schematic of the TFAB mathematical model, which contained two consecutive binding events that were decoupled, represented by $K_\alpha$ and $K_\beta$.
Figure 21:
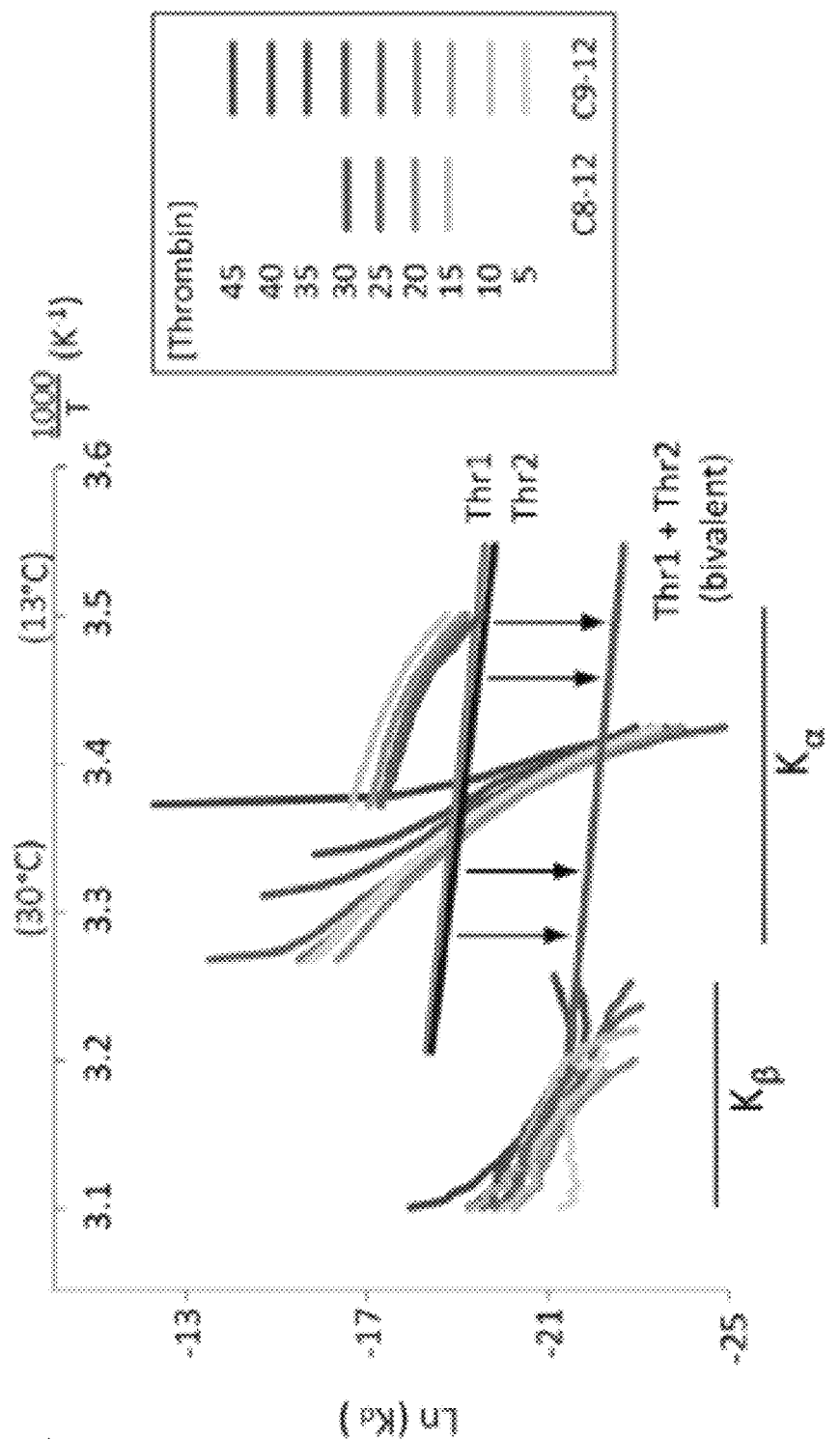
FIG. 21 shows a Van't Hoff plot showing thrombin TFAB processed through the model system demonstrated in FIG. 20.

A simple segmented model of TFAB can be constructed. FIG. 20 shows the segmented model of TFAB. The model was constructed based on the following assumptions; 1. At the beginning of thermal scanning, all target molecules are recognized by a pair of probes and these signal complexes are not dissociated while background complexes are dissociated. 2. Signal complexes start to be dissociated after the complete dissociation of background complexes. With the model, the thermodynamics of the TFAB were simulated. The simulation of the thermodynamics along with fitting of experimental data to our model is demonstrated in FIG. 21. Further model details are included in FIG. 30.

Figure 35A:
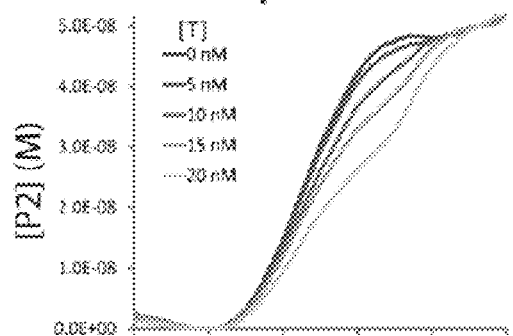
FIGS. 35A-35D demonstrate modeling (FIGS. 35C and 35D) of the TFAB signal and background complexes and thermodynamics. Also shown are experimental results that confirm the validity of the model (FIGS. 35A-35B), matching very closely with the model results.
Figure 35C:
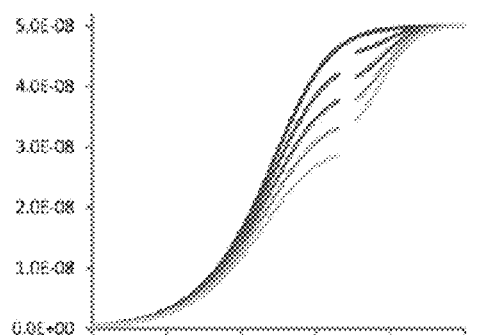
Figure 35B:
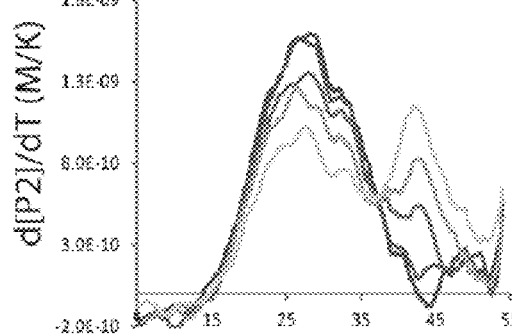
Figure 35D:
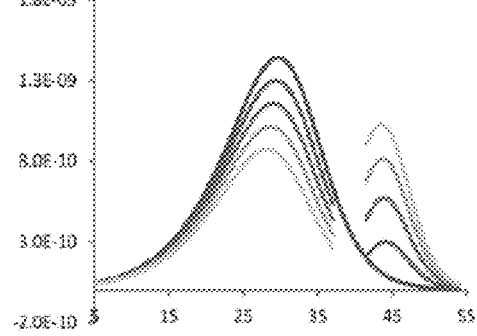
Figure 36:
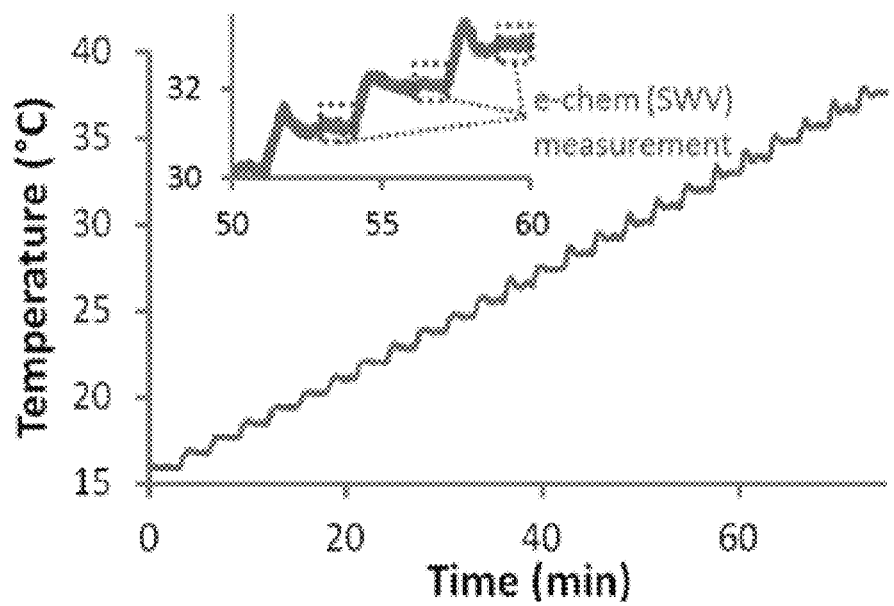
FIG. 36 shows a graph demonstrating thermistor recorded temperature data confirming accurate temperature control of the electrochemical cell shown in FIG. 11.

FIG. 35A demonstrates an experimental result of a fluorescence melting curve that was normalized to free P2 only, which allowed quantitative measurement of [P2] at a given temperature. FIG. 35B shows the derivative of the data in FIG. 35A. To compare to this experimental data, the segmented model expresses equilibrium constants ($K_\alpha$ and $K_\beta$) as a function of [P2], which allowed fitting of data to thermodynamic parameters using the temperature dependence of equilibrium constants. As seen in the model predictions in FIG. 35C-D, the model's assumptions are by definition segmented into low and high temperature regions, which prevents fitting of complete data sets, and the model breaks down at [T]>0.2[P1]. The initial assumptions ignore several important possibilities such as parallel binding pathways and protein dependent disassembly of signal complexes at high [P]. However, analytical solutions to the background (quadratic) and signal (cubic) expressions do exist, and these match qualitatively and quantitatively with the data. As such, this model can be used to predict optimal assay conditions with varying aptamer affinities ($K_\beta = K_{P1} \times K_{P2}$), and this modeling can be correlated with experiments. This model can be retro-fitted after a single measurement. As can be gleaned from comparison of melting curves in FIG. 35A (experiment) to FIG. 35C (model) and by comparison of derivative curves in FIG. 35B (experiment) to FIG. 35D (model), the mathematical model (FIGS. 20 and 30) nicely predicts the experimental results of the TFAB system. This correlation confirmed that measured signal transitions in TFAB were dominated by our predesigned DNA melting events and helped to confirm our mechanistic assertions in FIGS. 1-2 and FIGS. 12-13.

The background portion of this model was further validated through comparison to calculations using DNA nearest-neighbor thermodynamics [SantaLucia 1998]. With the 9-12 connector length, calculations gave $\Delta H = 265$ kJ mol-1 and $\Delta S = 0.767$ kJ mol-1 K-1, and fits of our model to the background peak in TFAB data gave similar values of $\Delta H = 257$ kJ mol-1 and $\Delta S = 0.708$ kJ mol-1 K-1.

Example 5

Figure 33:
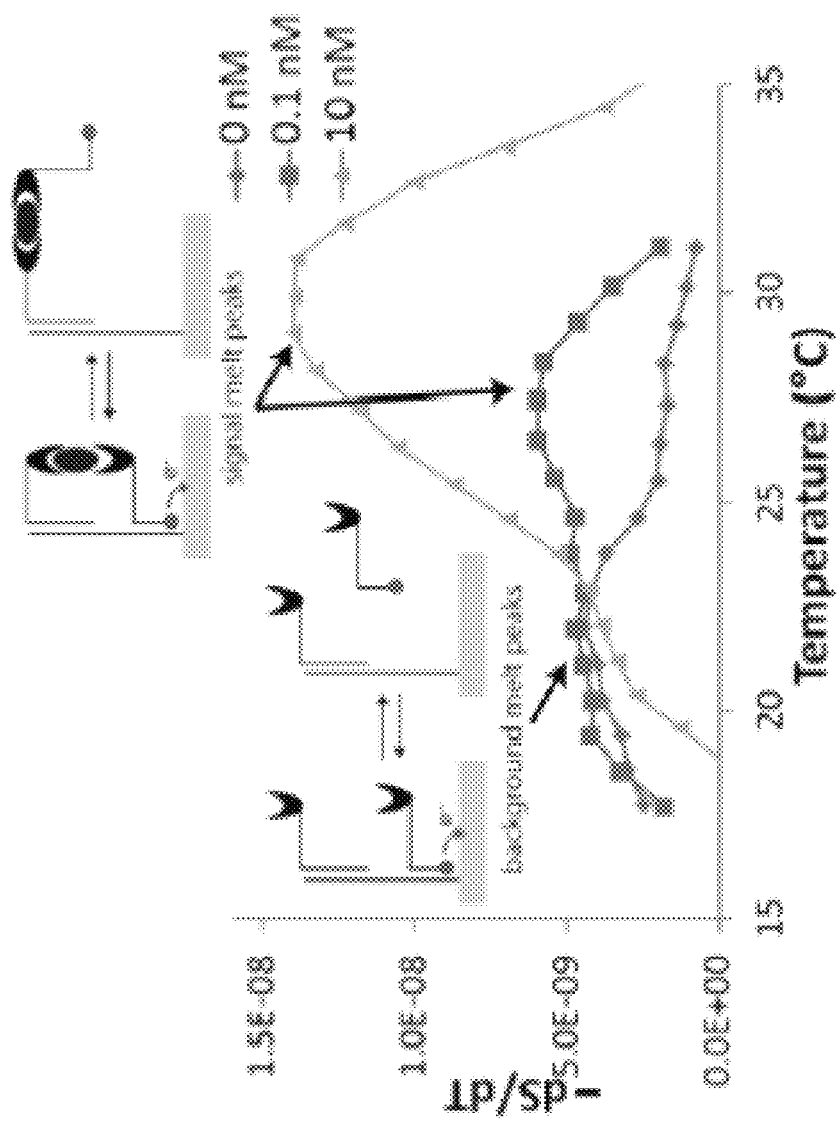
FIG. 33 shows a graph demonstrating the signal and background melt peaks for a thermal scanning ECPA (tsECPA) at different concentrations of the target protein (0 nM, 0.1 nM, and 10 nM).
Figure 34:
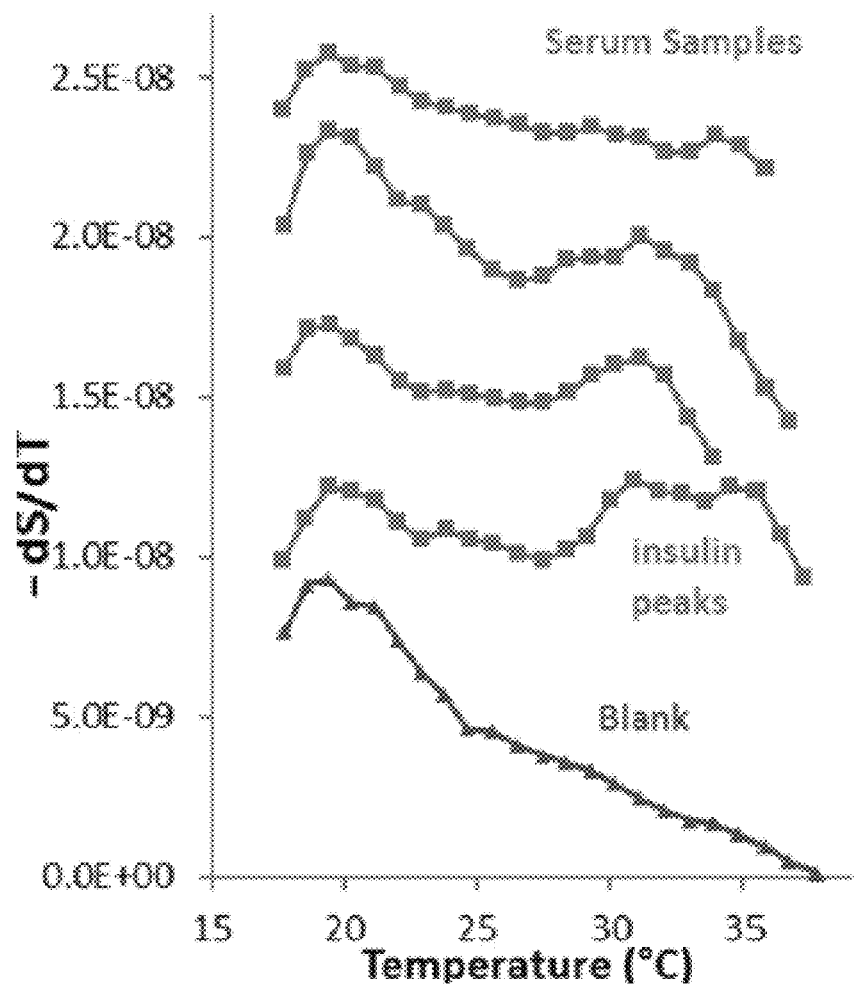
FIG. 34 shows a graph demonstrating the results of an insulin tsECPA for quantifying endogenous insulin in undiluted human serum.

Direct detection of endogenous insulin in human serum can be accomplished using electrochemistry. Our previously developed electrochemical proximity assay (ECPA) (Hu et al., 2012 JACS and Hu et al, 2014 JACS and U.S. Patent Application Publication 2014/0102915) is a direct-readout method for analyzing proteins in the femtomolar range. In ECPA, aptamer or antibody-oligonucleotide probes are used to selectively bind to specific proteins. By coupling this binding to other oligonucleotides, one can significantly increase the stability of hybridization of thiolated-DNA (immobilized on gold electrode) and methylene-blue labeled DNA (MB-DNA). Herein, a thermal scanning electrochemical proximity assay (tsECPA) was employed to detect insulin. A graphical representation demonstrating the signal and background melt peaks for a tsECPA is shown in FIG. 33, along with results generated with the thermally controlled electrochemical system shown in FIG. 11. Since background complexes melt at lower temperature, and signal complexes are stable even at higher temperature, analytical separation of signal and background is possible. The figure shows insulin quantification using antibody-oligonucleotide conjugate probes. SWV measurement was carried out between 15° C. and 37° C., at interval of 1° C. The signal peak in the −dS/dT plot shows a protein dependent increase.

Materials and Methods:

Antibody-oligonucleotide conjugates were prepared as described previously (C. J. DeJournette, J. Kim, H. Medlen, X. Li, L. J. Vincent, C. J. Easley, *Analytical chemistry* 2013, 85, 10556-10564). Conjugation and purification were accomplished using the Antibody-Oligonucleotide All-In-One Conjugation Kit (Solulink), according to the manufacturer's instructions. The final conjugate concentrations were determined via the BCA protein assay.

Example 6

A thrombin TFAB and insulin TFAB was performed and two-dimensional heat maps were generated. The results are demonstrated in FIGS. 14A-C and 15A-C. The aptamer-based map for thrombin detection was collected by varying the temperature from 5 to 55° C. with a 0.5° C. interval and by varying protein concentration stepwise from 0 to 70 nM with a 5 nM interval. Heat maps (top to bottom) include background corrected the first derivative over temperature (dF/dT). Antibody-oligo based map for insulin detection from 0 to 6.5 nM in 0.5 nM increments. Thermofluorimetric maps were created using ImageJ. A two-dimensional text file of fluorescence intensity values (conc. as x-axis; T as y-axis) was imported as a Text Image and processed first with a two-pixel Gaussian blur filter. Partial derivative images were then created using 3×3 convolution filters; e.g. dF/dT matrix={−1,−1,−1; 0,0,0; 1,1,1}. Images were finally scaled to a square aspect ratio and displayed using a "fire" lookup table for ease of visualization.

Materials and methods. Generation of two-dimensional thermofluorimetric maps: The aptamer-based map for thrombin detection was collected by varying the temperature from 5 to 55° C. with a 0.5° C. interval and by varying protein concentration stepwise from 0 to 70 nM with a 5 nM interval. Heat maps (top to bottom) include background corrected the first derivative over temperature (dF/dT). Antibody-oligo based map for insulin detection from 0 to 6.5 nM in 0.5 nM increments. Thermofluorimetric maps were created using ImageJ. A two-dimensional text file of fluorescence intensity values (conc. as x-axis; T as y-axis) was imported as a Text Image and processed first with a two-pixel Gaussian blur filter. Partial derivative images were then created using 3×3 convolution filters; e.g. dF/dT matrix={−1,−1,−1; 0,0,0; 1,1,1}. Images were finally scaled to a square aspect ratio and displayed using a "fire" lookup table for ease of visualization. Thermofluorimetric maps are shown in FIGS. 14A-C and 15A-C.

Example 7

The TFAB can minimize autofluoresence in human serum samples, which can permit one-step, mix-and-read fluorescence protein assays in a complex biological matrix. As shown in FIG. 28, standard fluorescence assays in human serum were previously not possible (standard fluorescence) due to the intense interference from autofluorescence (665 nm emission). However the TFAB was observed to allow sensitive detection of insulin in human serum using antibody-oligonucleotide conjugate probes. To test applicability of TFAB in human serum samples, insulin at a series of concentrations were spiked in diluted human serum samples before being subjected to TFAB.

Materials and methods for this work are identical to that described in Example 3 above.

Example 8

Thermal scanning is not a standard feature in electrochemical systems. In this Example a custom temperature control system that is coupled with a standard three-electrode electrochemical cell is demonstrated. As shown in FIGS. 11, 33, 36, and 37, a customized thermal regulator was created to control the temperature of the electrochemical cell between ~10 to 80° C. The system was designed with an integrated Peltier control module, capable of delivering 2.2 A at up to 5 V. A 30 mm×30 mm Peltier unit capable of sustaining a 66° C. temperature difference was used to for the thermal pumping, and a thermistor was used for temperature measurements. The opposing side of the Peltier module was fitted with a heat sink with cooling fins and an electric fan (airflow of 3.7 ft$^3$ min$^{-1}$). The controller was driven with an in-house written LabVIEW application, which integrates safety shutdown procedures, digital proportional-integral-derivative (PID) control, and data capture functionality. The LabVIEW app was also interfaced with the potentiostat to trigger voltammetric scanning after the electrochemical cell had thermally equilibrated at each set temperature (see graph inset). As shown by the thermistor recorded data in FIG. 36, PID constants were optimized for ramping and stabilizing of the cell's temperature at 1° C. increments with precise feedback control.

Figure 37:
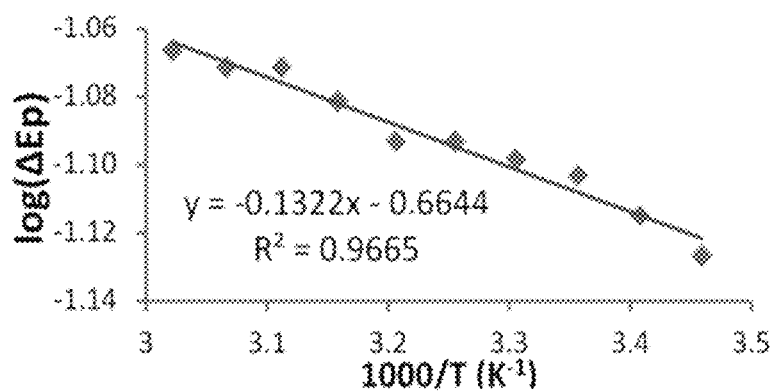
FIG. 37 shows a graph demonstrating predictable temperature dependences of electrochemistry in the thermally controlled cell. Cyclic voltammograms of $Ru(NH_3)_6^{2+}$ at the gold electrodes were collected from 15° C. to 60° C. at intervals of about 5° C. The difference between the anodic and cathodic peak potentials, $\Delta E_p$, was used as a measure of the electron transfer rate constant. The plot of $\log(\Delta E_p)$ vs $1/T$ shows a linear Arrhenius behavior, as expected.

The robustness of the temperature-controlled cell was first confirmed through study of electron transfer behavior of $Ru(NH_3)_6^{2+}$ at the gold electrodes. Cyclic voltammograms were collected on a temperature range from approximately 15° C. to 60° C. at intervals of about 5° C. In these experiments, the goal was to demonstrate the Arrhenius behavior of the $Ru(NH_3)_6^{2+}$ electron transfer kinetics, using classical treatments in temperature dependent rates [Nicholson 1965]. The difference between the anodic and cathodic peak potentials, $\Delta E_p$, as a measure of the electron transfer rate constant was used. In FIG. 37, which shows $\log(\Delta E_p)$ vs 1/T, and the data show a linear Arrhenius behavior, as expected. This evidence supports the assertion that the temperature control circuitry and cell are well behaved and well characterized.

Example 9

Figure 22:
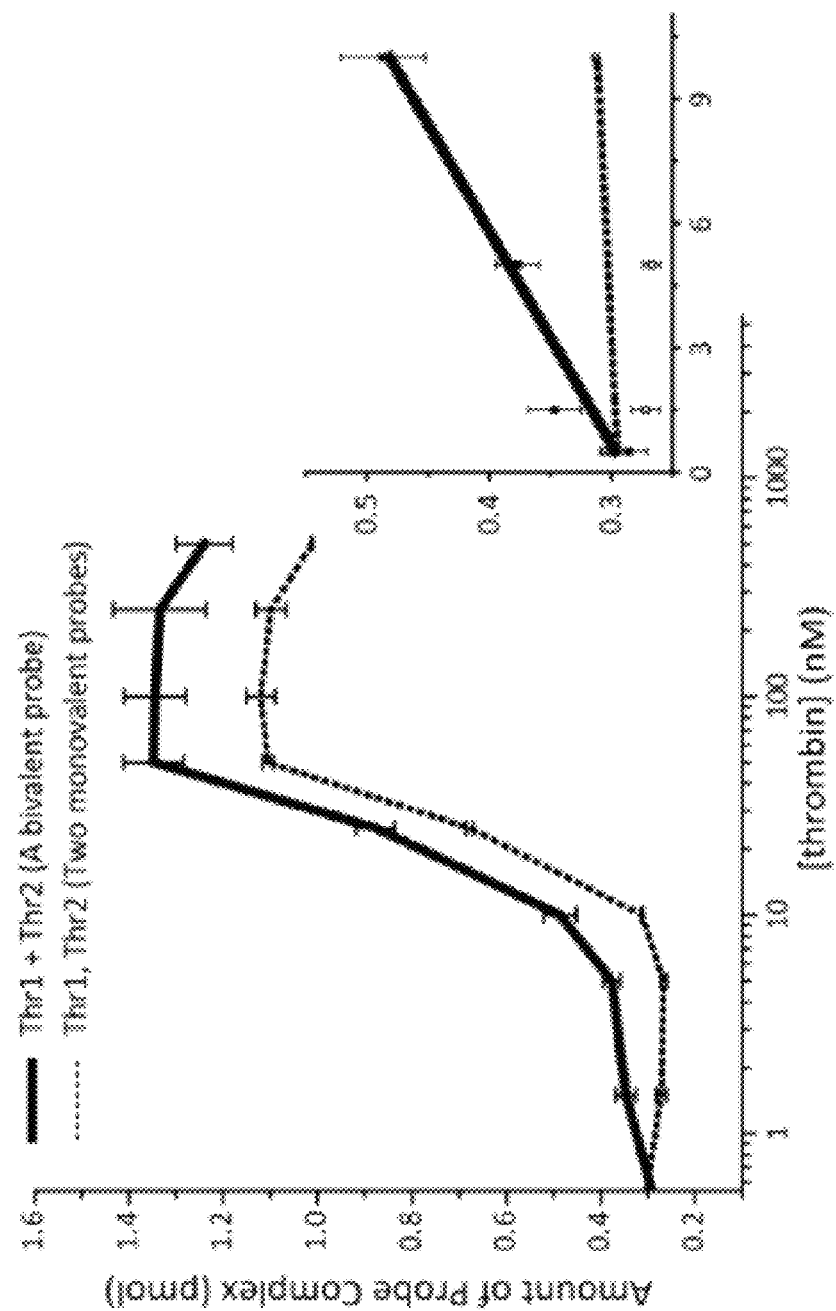
FIG. 22 shows a graph demonstrating a comparison of novel isothermal bivalent assay (solid line) with its monovalent counterpart (dotted line) showed an order-of-magnitude improvement in dynamic range with bivalent probes.
Figure 31:
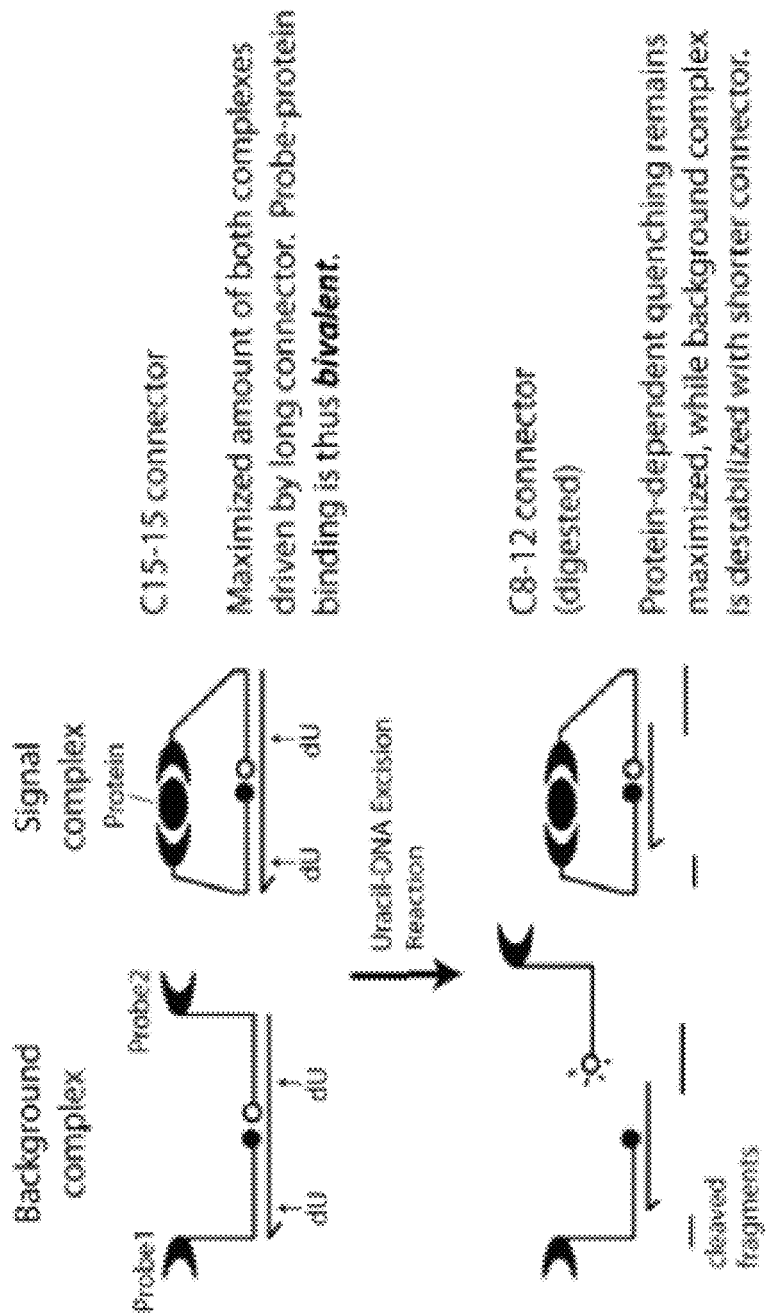
FIG. 31 shows a schematic of isothermal bivalent fluorescence assay.
Figure 32A:
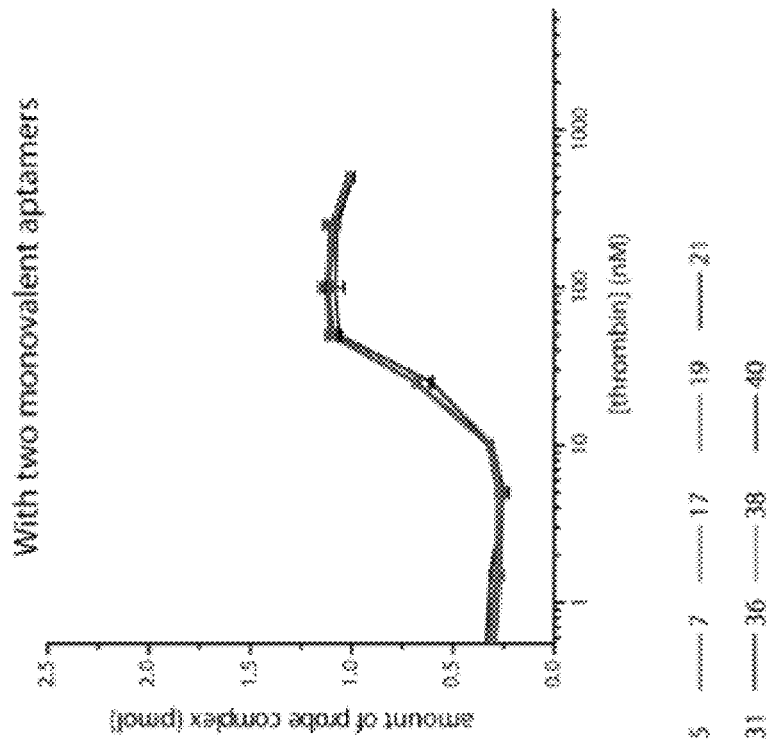
FIGS. 32A and 32B show graphs demonstrating isothermal bivalent fluorescence assay. Conversion of C15-15 connector to C8-12 connector by the Uracil-DNA Excision Mix was monitored by thrombin FPA (32A). As the reaction reached completion over ~30 min, background complexes were destabilized, while much of the signal complexes remained intact. This is evidenced by the emergence of protein-dependent signal over time. By starting with the C8-12 connector (without bivalent probes), probe-target equilibrium had been established from the beginning of the excision reaction, thus there was no change over time, as expected (FIG. 32B).
Figure 32B:
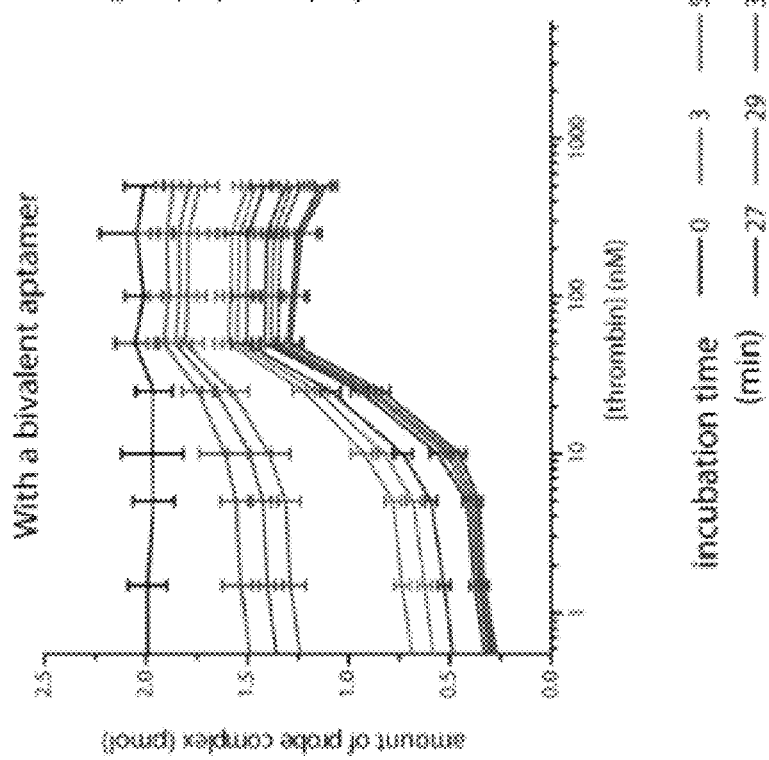

With enhanced understanding given by the model, an isothermal mimic of TFAB was created that again leveraged probe bivalency for maximizing signal and removing background. In stepwise fashion, (I) the bivalent probe was further stabilized with a longer DNA connector at room temperature, (2) added protein analyte, and (3) destabilized the complexes by enzymatically shortening the connector. This way, it was reasoned that protein-stabilized signal complexes would remain intact while the background complexes would melt. To achieve selective destabilization of the connector/probe hybridization, we strategically placed cleavable deoxyuridines (dU) into the connector oligonucleotide. A long connector (C15-15) could thus be digested into a shorter connector (C8-12) through enzymatic cleavage of dUs with Uracil-DNA Excision Mix. A schematic of this assay is given in FIG. 31 alongside kinetic characterization of the cleavage reaction (32A-B). FIG. 22 compares this isothermal bivalent assay and its monovalent counterpart. Indeed, the bivalent assay exhibited higher total amounts of signal complexes at all protein concentrations as well as higher sensitivity at low protein concentrations (<10 nM).

Example 10

Figure 25:
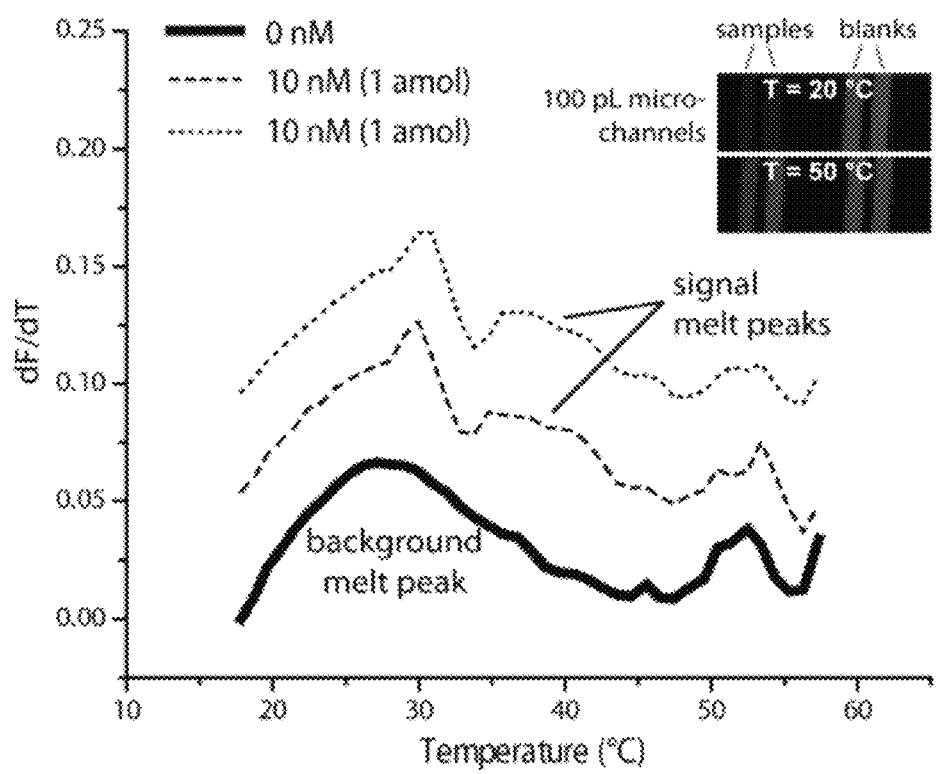
FIG. 25 shows a graph demonstrating the assay performance results of a miniaturized TFAB. Miniaturization allowed direct fluorescence quantification of only 1 amol of Thrombin.

By introducing time-stable, thermal gradients, both versions of our assays (TFAB and tsECPA) could be accomplished without waiting for thermal scanning, enabling "instant" readout that will be limited only by probe/target binding equilibria and SWV readout. Drawing from analogous thermogravimetry, it can then be possible to directly quantify proteins with a calibration-free, rapid imaging of the response in the thermal gradient. Importantly, it is shown in FIG. 25 that TFAB is functional in micro channels of only 100 picoliter volume, when using standard thermal scanning over time. This result is encouraging for the proposed gradient microfluidic TFAB (FIG. 10).

A design of gradient microfluidic TFAB is shown in FIG. 10. Miniature Peltier elements (5-mm) can be used to create a thermal gradient along an aluminum block, which will be translated through a thin glass coverslip floor (good thermal conductivity) to aqueous solution within microfluidic channels. The microfluidic devices will be fabricated in polydimethylsiloxane. (PDMS), which is thermally insulating. Insulating material (not shown in figure) can also be added surrounding the Peltier elements and metal block. To rapidly evaluate the thermal gradient integrity in each design iteration, a thermal imaging camera (FLIR E50bx MSX) with sub-millimeter image resolution can be employed. This could allow empirical optimization in real-time, compared to more time-consuming and possibly inaccurate thermal simulations.

The temperature resolution of this system will thus be defined by the number of channels packed into the thermal gradient. With a gradient from 10-60° C., over a distance of 20 mm, a resolution of 0.5° C. it would be possible using 100 microfluidic channels of 100 µm width and 100 µm spacing. Samples can be introduced in parallel into all channels, and fabrication can be accomplished using photolithography. A standard fluorescence microscope can be used for imaging and image analysis can be accomplished using ImageJ.

We claim:

1. A method of target molecule detection comprising:
    contacting a sample with a first probe, wherein the first probe is configured to bind a target molecule;
    contacting the sample with a second probe, wherein the second probe is configured to bind the target molecule;
    forming a signal complex, wherein the signal complex comprises a target molecule that is bound to the first probe and the second probe;
    forming a background complex, wherein the background complex does not comprise a target molecule that is simultaneously bound to the first probe and the second probe;
    thermally scanning the signal complex and the background complex to form a temperature melting curve, the temperature melting curve comprising:
        a first melting temperature peak, wherein the first melting temperature peak corresponds to the melting temperature of the signal complex; and
        a second melting temperature peak, wherein the second melting temperature peak corresponds to the melting temperature of the background complex; and
    detecting the target molecule via measuring a characteristic of the first melting temperature peak.

2. The method of claim 1, further comprising quantifying the amount of signal complex by the peak area of the first melting temperature peak.

3. The method of claim 1, wherein the first probe is selected from the group consisting of: aptamers, antibodies or fragments thereof, proteins, and oligonucleotides.

4. The method of claim 1, wherein the second probe is selected from the group consisting of: aptamers, antibodies or fragments thereof, proteins, and oligonucleotides.

5. The method of claim 4, wherein the first probe and the second probe are each directly bound to the target molecule in the signal complex.

6. The method of claim 5, wherein the first probe and the second probe are each selected from the group consisting of: aptamers, antibodies or fragments thereof, proteins, and oligonucleotides.

7. The method of claim 6, further comprising contacting the signal complex with an intercalating agent.

8. The method of claim 7, wherein the step of thermally scanning further comprises measuring a signal produced by the intercalating agent.

9. The method of claim 6, wherein the first probe, the second probe, or each of the first and the second probes comprise an optically active molecule.

10. The method of claim 9, wherein the step of thermally scanning further comprises measuring a signal produced by the optically active molecule.

11. The method of claim 5, further comprising contacting the sample with a proximity oligonucleotide.

12. The method of claim 11, wherein the first probe is configured to bind the target molecule and the proximity oligonucleotide.

13. The method of claim 12, wherein the second probe is configured to bind the target protein and the proximity oligonucleotide, and wherein the first and the second probes form a paired bivalent probe.

14. The method of claim 13, wherein the first probe and the second probe each comprise a protein binding moiety independently selected the group consisting of: aptamers, antibodies or fragments thereof, proteins, and oligonucleotides.

15. The method of claim 14, wherein the binding moiety is an antibody or a fragment thereof and wherein the antibody or a fragment thereof further comprises a connector oligonucleotide, wherein the connector oligonucleotide is coupled to the antibody or fragment thereof and is configured to bind the proximity nucleotide.

16. The method of claim 13, wherein the first probe comprises a quencher molecule.

17. The method of claim 16, wherein the second probe comprises an optically active molecule.

18. The method of claim 17, wherein the step of thermally scanning further comprises measuring a signal produced by the optically active molecule.

19. The method of claim 13, wherein the proximity oligonucleotide is coupled to an electrically conductive substrate.

20. The method of claim 19, wherein the first probe, the second probe, or each of the first probe and the second probe further comprises a redox-active molecule.

21. The method of claim 20, wherein the step of thermally scanning further comprises measuring the current produced by the electrically conductive substrate.

22. The method of claim 12, further comprising contacting the sample with a connector oligonucleotide, wherein the connector oligonucleotide is configured to bind the proximity oligonucleotide.

23. The method of claim 22, wherein the second probe is configured to bind the target molecule and the connector oligonucleotide.

24. The method of claim 23, wherein the proximity oligonucleotide is coupled to an electrically conductive substrate.

25. The method of claim 24, wherein the first probe, the second probe, the connector oligonucleotide, or combinations thereof, further comprise a redox active molecule.

26. The method of claim 25, wherein the step of thermally scanning further comprises measuring the current produced by the electrically conductive substrate.

* * * * *

SEQUENCE LISTING

<160> NUMBER OF SEQ ID NOS: 16

<210> SEQ ID NO 1
<211> LENGTH: 60
<212> TYPE: DNA
<213> ORGANISM: Artificial Sequence
<220> FEATURE:
<223> OTHER INFORMATION: Thr1_BFQ

<400> SEQUENCE: 1
cagtccgtgg tagggcaggt tggggtgact tttactttct gcacgacact ttggaacagc      60

<210> SEQ ID NO 2
<211> LENGTH: 60
<212> TYPE: DNA
<213> ORGANISM: Artificial Sequence
<220> FEATURE:
<223> OTHER INFORMATION: Thr2_TAMARA

<400> SEQUENCE: 2
aataacgtca gaatcgtact cgggtgtgac tactggttgg tgaggttggg tagtcacaaa      60

<210> SEQ ID NO 3
<211> LENGTH: 21
<212> TYPE: DNA
<213> ORGANISM: Artificial Sequence
<220> FEATURE:
<223> OTHER INFORMATION: C9-12 connector for thrombin thermofluorimetric analysis of bivalent probes

<400> SEQUENCE: 3
gacgttattg ctgttccaaa g                                         21

<210> SEQ ID NO 4
<211> LENGTH: 20
<212> TYPE: DNA
<213> ORGANISM: Artificial Sequence
<220> FEATURE:
<223> OTHER INFORMATION: C8-12 connector for thrombin thermofluorimetric analysis of bivalent probes

<400> SEQUENCE: 4
acgttattgc tgttccaaag                                           20

<210> SEQ ID NO 5
<211> LENGTH: 19
<212> TYPE: DNA
<213> ORGANISM: Artificial Sequence
<220> FEATURE:
<223> OTHER INFORMATION: C7-12 connector for thrombin thermofluorimetric analysis of bivalent probes

<400> SEQUENCE: 5
cgttattgct gttccaaag                                            19

<210> SEQ ID NO 6
<211> LENGTH: 47
<212> TYPE: DNA
<213> ORGANISM: Artificial Sequence
<220> FEATURE:
<223> OTHER INFORMATION: AbA_BHQ2

<400> SEQUENCE: 6
tcgtggaact atctagcggt gtacgtgagt gggcatgtag caagagg              47

<210> SEQ ID NO 7
<211> LENGTH: 46
<212> TYPE: DNA
<213> ORGANISM: Artificial Sequence
<220> FEATURE:
<223> OTHER INFORMATION: AbB_TYE66

<400> SEQUENCE: 7
tcgtggaact atctagcggt gtacgtgagt gggcatgagc aagagg               46

<210> SEQ ID NO 8
<211> LENGTH: 47
<212> TYPE: DNA
<213> ORGANISM: Artificial Sequence
<220> FEATURE:
<223> OTHER INFORMATION: AbA_BFQ

<400> SEQUENCE: 8
tcgtggaact atctagcggt gtacgtgagt gggcatgtag caagagg              47

<210> SEQ ID NO 9
<211> LENGTH: 39
<212> TYPE: DNA

```
<213> ORGANISM: Artificial Sequence
<220> FEATURE:
<223> OTHER INFORMATION: AbB_TAMARA

<400> SEQUENCE: 9
gtcatcattc gaatcgtact gcaatcgggt attaggcta                                    39

<210> SEQ ID NO 10
<211> LENGTH: 20
<212> TYPE: DNA
<213> ORGANISM: Artificial Sequence
<220> FEATURE:
<223> OTHER INFORMATION: C'10-10 connector for insulin
      thermofluorimetric analysis of bivalent probes

<400> SEQUENCE: 10
gaatgatgac cctcttgcta                                                         20

<210> SEQ ID NO 11
<211> LENGTH: 18
<212> TYPE: DNA
<213> ORGANISM: Artificial Sequence
<220> FEATURE:
<223> OTHER INFORMATION: C'10-8 connector for insulin thermofluorimetric
      analysis of bivalent probes

<400> SEQUENCE: 11
atgatgaccc tcttgcta                                                           18

<210> SEQ ID NO 12
<211> LENGTH: 17
<212> TYPE: DNA
<213> ORGANISM: Artificial Sequence
<220> FEATURE:
<223> OTHER INFORMATION: C'10-7 connector for insulin thermofluorimetric
      analysis of bivalent probes

<400> SEQUENCE: 12
tgatgaccct cttgcta                                                            17

<210> SEQ ID NO 13
<211> LENGTH: 60
<212> TYPE: DNA
<213> ORGANISM: Artificial Sequence
<220> FEATURE:
<223> OTHER INFORMATION: Thr1_BFQ

<400> SEQUENCE: 13
cagtccgtgg tagggcaggt tggggtgact tttactttct gcacgacact ttggaacagc             60

<210> SEQ ID NO 14
<211> LENGTH: 60
<212> TYPE: DNA
<213> ORGANISM: Artificial Sequence
<220> FEATURE:
<223> OTHER INFORMATION: Thr2_TAMARA

<400> SEQUENCE: 14
aataacgtca gaatcgtact cgggtgtgac tactggttgg tgaggttggg tagtcacaaa             60

<210> SEQ ID NO 15
<211> LENGTH: 30
<212> TYPE: DNA
<213> ORGANISM: Artificial Sequence
<220> FEATURE:
<223> OTHER INFORMATION: C15-15 - connector for isothermal thrombin
      assay with a bivalent probe. contains deoxyuridine at nucleotides7
```

```
         and 28

<400> SEQUENCE: 15
gattctuacg ttattgctgt tccaaagugt                                              30

<210> SEQ ID NO 16
<211> LENGTH: 20
<212> TYPE: DNA
<213> ORGANISM: Artificial Sequence
<220> FEATURE:
<223> OTHER INFORMATION: C8-12 connector for isothermal thrombin assay
      with a bivalent probe

<400> SEQUENCE: 16
acgttattgc tgttccaaag                                                         20
```